(12) United States Patent
MacKenzie et al.

(10) Patent No.: US 7,223,901 B2
(45) Date of Patent: May 29, 2007

(54) SOYBEAN FGAM SYNTHASE PROMOTERS USEFUL IN NEMATODE CONTROL

(75) Inventors: Sally MacKenzie, Lincoln, NE (US); Zarir Vaghchhipawala, Ardmore, OK (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 75 days.

(21) Appl. No.: 11/091,668

(22) Filed: Mar. 28, 2005

(65) Prior Publication Data
US 2005/0262585 A1    Nov. 24, 2005

Related U.S. Application Data

(60) Provisional application No. 60/556,745, filed on Mar. 26, 2004.

(51) Int. Cl.
*C12N 15/09* (2006.01)
*C12N 15/82* (2006.01)
*A01H 5/00* (2006.01)

(52) U.S. Cl. .............. 800/279; 800/287; 800/278; 800/298; 800/312; 536/24.1; 435/468; 435/320.1; 435/419

(58) Field of Classification Search .......... 800/278, 800/279, 312; 536/24.1; 435/468, 69.1
See application file for complete search history.

(56) References Cited

U.S. PATENT DOCUMENTS

| 5,651,965 | A | 7/1997 | Payne |
| 6,271,437 | B1 * | 8/2001 | Jessen et al. ............... 800/278 |
| 2004/0006791 | A1 | 1/2004 | Davis, et al. |

OTHER PUBLICATIONS

Kim et al. Plant Molecular Biology, Biology, vol. 24, pp. 105-117, 1994.*
Benfey et al. Science 1990, vol. 250, pp. 959-966.*
Keller et al. The Plant Cell, vol. 3, pp. 1051-1061, 1991.*
Atkinson, et al., 2003. Engineering Plants for Nematode Resistance, Annu. Rev. Phytopathol. 41:615-639.
Biondi, et al., Jun. 2004. Evaluation of Nostoc Strain ATCC 53789 as a Potential Source of Natural Pesticides. Applied and Environmental Microbiology. 70(6):3313-3320.

* cited by examiner

*Primary Examiner*—Medina A. Ibrahim
(74) *Attorney, Agent, or Firm*—Jondle & Associates P.C.

(57) ABSTRACT

The subject invention relates to nematode responsive domains obtained from soybean promoters for phosphoribosylformylglycinamidine ribonucleotide (FGAM) synthase paralogs. The nematode responsive domains can be used in promoters that are linked to heterologous DNA. Such constructs can be expressed in transfected or transformed soybean and used in the control of nematode infection of soybean.

10 Claims, 16 Drawing Sheets

```
ttgtttttta ttttttaaaa aagttttgac atgtacctgt aatataatat ccatgtagga    60
ggcttttta  acaactgtat cccatataac atatcatgtg agaatctata gtccacttta   120
taagaatgtg tgaggtcagg tggattaaca tttaacaatt ttcctatttt cccatgcata   180
aaaaaaaaac atttatcaat ttttccacgt agtccatttt ttttaaaaaa agtaatgcga   240
catgtgaaat tgccatataa tgattttgat aggatgtctt aaaacagtct cattttaata   300
aaatatttta aaataatatc atttaattat tatttctaat tttgcctcaa ttttatcaat   360
cagttaaaga agtcacgaga ttttcatata tctattttat ttcaatattt aaattgaaac   420
tttcaattga ttttttatt  gtcattcatt ctgtaaccaa taaaattctt tgaattttt    480
gagattgatt tctcgtatgt taaattataa tatgacaaca ttatatttaa tttttcttaa   540
ttacaaagtt ttcaataaca aaattggatc garagaraat gtcatcatat agtaacttt    600
tttaagatg  acacataata acttgcactt taaaaaaaga cttgcactt gcagatcaag    660
grcataaatt aattttagc  atatgtctga atacgcgtta tcaaaaaata aatcaaacgt   720
ctaatgcaaa agtcactctc acaactcaca agtttctgtg tcttttggga agttgatgtt   780
aaaatgagag aatgaaccga tatatatata tatatatata tatatcaa   ttgcgatgtt   840
aagattatta ttgaagtaga cacatgacaa gatagaaaaa atttacttat aaaagaaaat   900
aataacatgc aaatgaatta tctcagtcaa gtaaaattt  taatttatta ttttttttgaa  960
aggcaaaaat ttaaatttat tatataagaa tgaatcttat actttatata actatagaag  1020
ataaagttat attgagatat tttaactcat tagttatcaa tttaacgatt tcaactttt   1080
ataaaccaca ggcaatttga tagaaacgtt aaaactttaa aagaaaatc  caaactgtac  1140
ttacagttcc cacagggcca attctaccta gagttttagt gaagagccaa ttctaatttt  1200
ttttcctcct ataaaatcaa atacacacat ttttaataaa agttttttt  taaatctaga  1260
ttacaaaaga gattctgaat taaaaatatt aaaagtcact tttcactgcg tttaaaagtc  1320
atacaattgg ctgtaaaaaa aaacagtcat acaattatta cattgcacca aatatacatc  1380
ttattattat ctgatatgaa ttaaatatta tacatgatta agtctatttt tgctcttatc  1440
ttatttatca tatattatta tttgatttat tatctttctt taaaaaaatc tcattcttat  1500
tttattttat catgttctta ttttgttgtc gactcctctc ttattttaac aagtttttca  1560
tagataataa ttttttttcat aaataaaagt taacgatact tgaaaatact tctcaaacta 1620
acactagttt ttactttttt ttttatttaa aaatatctta gtaatttaca gcttcgagtt  1680
tcacaaagaa acaagtgtgt ttatatatag gcttctttta tgaactttgg attacgcatc  1740
cgattcggct aaaaaaggta agcatcggca gacaaagaaa tcgtcgataa aacagagaaa  1800
```

Figure 1A- FGAM1

```
atataaaaat agcgccaacg caaccaatag ttaaattgaa agggtgaaaa cttttaatat    1860
ttttactcgt ttgatttgaa gggagagaaa gagagtacta agtggctagt agggttttat    1920
tgtgtgccac accaaaaccc tctcttcgtt ttacgtcact tccacactca ctctgttttg    1980
ttctgctact cttcgattct acttcttcta cttgattccc acatttctta ttttgcgtag    2040
tgaatatttt ttcttcttc ttttttaga gctttcccac acttgatcga ggatatggcg    2100
actgcgacgg aatttggggt atcgcaattc ttgaaggttt gattttaatt cctctcttgg    2160
aattaacctc atatgctgca cccctttttgt taatttatta attgttgttc ttgttggggg    2220
aaaaaggtca tgctttgatg ctgcagtgac atgtttcgat gcatctttgc ttattgggtt    2280
ttgtgatttt ggtttcaggg gacctccagg caaactctgt ttttgtagaa gaagcctcag    2340
aggcagaaaa gtcgcatgct ttggggtgca ctctggaatc ggaattgggg tctgggatca    2400
actcgcagag ctttgccttt aaggtgtcag actcaggaaa atcccagagc tgtggtttct    2460
ggtggcgtaa gcagttctgt agaggagcaa cctgccttgt ttgagaagcc cgcttccgaa    2520
gttgttcatt tgtaccgtgt cccgttt atg caa gaa agt gca gct gct gag ctt    2574
                                Met Gln Glu Ser Ala Ala Ala Glu Leu
                                 1               5
```

```
ttg aag gag gct caa gtg aaa atc tcc agt cag atc gtg gaa ata cta    2622
Leu Lys Glu Ala Gln Val Lys Ile Ser Ser Gln Ile Val Glu Ile Leu
 10              15                  20                  25 acg gag cag tgc tat aat gtt ggc ctt agt tcg caa ctt tcc ggt gga    2670
Thr Glu Gln Cys Tyr Asn Val Gly Leu Ser Ser Gln Leu Ser Gly Gly
             30                  35                  40 aaa ttt tca gtt ctt gga tgg ctt ctt caa gaa aca ttc gag cct gag    2718
Lys Phe Ser Val Leu Gly Trp Leu Leu Gln Glu Thr Phe Glu Pro Glu
                 45                  50                  55 aat ctg gga act gag agc ttt ctt gag aag aag agg aag gag ggt ctg    2766
Asn Leu Gly Thr Glu Ser Phe Leu Glu Lys Lys Arg Lys Glu Gly Leu
             60                  65                  70 att cca gtt att gtt gaa gtt ggc ccc agg ttg tca ttc acc aca gca    2814
Ile Pro Val Ile Val Glu Val Gly Pro Arg Leu Ser Phe Thr Thr Ala
 75                  80                  85 tgg tct act aat gct gtt gca att tgc cag gcc tgt ggt ttg aca gaa    2862
Trp Ser Thr Asn Ala Val Ala Ile Cys Gln Ala Cys Gly Leu Thr Glu
 90                  95                 100                 105 gtt aac cgt ttg gaa cgg tca agg agg tac ttg ttg ttc acc acc act    2910
Val Asn Arg Leu Glu Arg Ser Arg Arg Tyr Leu Leu Phe Thr Thr Thr
             110                 115                 120 gaa ctg caa gat tat caa atc aat gat ttt gca tct atg gtg cat gat    2958
Glu Leu Gln Asp Tyr Gln Ile Asn Asp Phe Ala Ser Met Val His Asp
             125                 130                 135
```

Figure 1A Cont.- FGAM1

```
agg atg act gaa tgt gtt tat att cag aaa cta aca tcc ttt gag acc        3006
Arg Met Thr Glu Cys Val Tyr Ile Gln Lys Leu Thr Ser Phe Glu Thr
    140                 145                 150 agt gtt gtt ccg gag gag att cat tat ata cct gtc atg gag agg gga        3054
Ser Val Val Pro Glu Glu Ile His Tyr Ile Pro Val Met Glu Arg Gly
    155                 160                 165 cga aag gca tta gaa gag att aat ttg gag atg ggt ttt gcc ttt gat        3102
Arg Lys Ala Leu Glu Glu Ile Asn Leu Glu Met Gly Phe Ala Phe Asp
170                 175                 180                 185 gac cag gat tta gaa tac tac acc aaa ctt ttc aga gaa gac att aag        3150
Asp Gln Asp Leu Glu Tyr Tyr Thr Lys Leu Phe Arg Glu Asp Ile Lys
                190                 195                 200 cgc aac ccg aca aat gtg gaa ttg ttt gat ata gca cag tcc aac agt        3198
Arg Asn Pro Thr Asn Val Glu Leu Phe Asp Ile Ala Gln Ser Asn Ser
            205                 210                 215 gag cac agc aga cac tgg ttt ttt act gga aag att ttc att gat gga        3246
Glu His Ser Arg His Trp Phe Phe Thr Gly Lys Ile Phe Ile Asp Gly
            220                 225                 230 cag ccc gtg aat aga act ctc atg cag att gtg aaa agt act ctg cag        3294
Gln Pro Val Asn Arg Thr Leu Met Gln Ile Val Lys Ser Thr Leu Gln
        235                 240                 245 gca aac cca aat aac tca gtt att ggc ttc aag gat aac tct agt gca        3342
Ala Asn Pro Asn Asn Ser Val Ile Gly Phe Lys Asp Asn Ser Ser Ala
250                 255                 260                 265 atc agg ggt tth cca gtg aag cag ctc cga cca gtt cag cct ggt tca        3390
Ile Arg Gly Xaa Pro Val Lys Gln Leu Arg Pro Val Gln Pro Gly Ser
                270                 275                 280 gca tgt cca tta gaa gtt gca gtc cat gag tta gat atc ttg ttt aca        3438
Ala Cys Pro Leu Glu Val Ala Val His Glu Leu Asp Ile Leu Phe Thr
            285                 290                 295 gct gaa aca cat aat ttt cca tgc gca gtg gca cct tat cct ggt gca        3486
Ala Glu Thr His Asn Phe Pro Cys Ala Val Ala Pro Tyr Pro Gly Ala
            300                 305                 310 gag acg ggt gca gga ggt cgc att agg gat aca cac gct acc gga agg        3534
Glu Thr Gly Ala Gly Gly Arg Ile Arg Asp Thr His Ala Thr Gly Arg
        315                 320                 325 ggg tcc ttt gtc cag gca gct aca gct ggt tat tgc gtt ggg aat ctc        3582
Gly Ser Phe Val Gln Ala Ala Thr Ala Gly Tyr Cys Val Gly Asn Leu
330                 335                 340                 345 aac aca ccg ggc ttt tat gct cca tgg gaa gat ccc tcc ttt act tat        3630
Asn Thr Pro Gly Phe Tyr Ala Pro Trp Glu Asp Pro Ser Phe Thr Tyr
                350                 355                 360 cca tca aat ttg gca cca cct tta cag att ctg ata gat tct agt aat        3678
Pro Ser Asn Leu Ala Pro Pro Leu Gln Ile Leu Ile Asp Ser Ser Asn
            365                 370                 375
```

Figure 1A Cont.- FGAM1

| | | |
|---|---|---|
| ggt gca tct gac tat ggg aac aaa ttt gga gag cca ttg atc cag ggt<br>Gly Ala Ser Asp Tyr Gly Asn Lys Phe Gly Glu Pro Leu Ile Gln Gly<br>    380              385              390 | | 3726 |
| ttc tgt aga act ttc gga atg aga ctt cct ggt ggg gag agg cga gaa<br>Phe Cys Arg Thr Phe Gly Met Arg Leu Pro Gly Gly Glu Arg Arg Glu<br>395              400              405 | | 3774 |
| tgg ttg aag cca atc atg ttc agc gca ggc ata gga cag att gac cac<br>Trp Leu Lys Pro Ile Met Phe Ser Ala Gly Ile Gly Gln Ile Asp His<br>410              415              420              425 | | 3822 |
| ctt cat ata tca aag gga gag cct gac att ggg atg ctg gtt gtt aag<br>Leu His Ile Ser Lys Gly Glu Pro Asp Ile Gly Met Leu Val Val Lys<br>              430              435              440 | | 3870 |
| att gga ggc ccg gct tat cgt att ggt atg gga ggt ggg gca gcc tca<br>Ile Gly Gly Pro Ala Tyr Arg Ile Gly Met Gly Gly Gly Ala Ala Ser<br>              445              450              455 | | 3918 |
| agc atg gtc gat ggg cag aat gat gca gag ctt gat ttc aat gct gtg<br>Ser Met Val Asp Gly Gln Asn Asp Ala Glu Leu Asp Phe Asn Ala Val<br>              460              465              470 | | 3966 |
| caa cgt ggg gat gct gag atg gct caa aaa cta tat cgt ctt gtg cgt<br>Gln Arg Gly Asp Ala Glu Met Ala Gln Lys Leu Tyr Arg Leu Val Arg<br>475              480              485 | | 4014 |
| gct tgt att gag atg ggg gat aaa aac cca att atc agc att cat gat<br>Ala Cys Ile Glu Met Gly Asp Lys Asn Pro Ile Ile Ser Ile His Asp<br>490              495              500              505 | | 4062 |
| cag gga gct ggt ggg aac tgc aat gtt gta aag gaa att ata tat ccg<br>Gln Gly Ala Gly Gly Asn Cys Asn Val Val Lys Glu Ile Ile Tyr Pro<br>              510              515              520 | | 4110 |
| aag ggt gct gag ata gat gtc cga gca att gtg gtt ggt gat cat aca<br>Lys Gly Ala Glu Ile Asp Val Arg Ala Ile Val Val Gly Asp His Thr<br>              525              530              535 | | 4158 |
| atg tct gtt cta gaa att tgg ggt gca gag tat cag gag cag gat gca<br>Met Ser Val Leu Glu Ile Trp Gly Ala Glu Tyr Gln Glu Gln Asp Ala<br>              540              545              550 | | 4206 |
| atc tta gtg aag cct gaa agc cgt gat ctc cta gaa tca atc tgt aac<br>Ile Leu Val Lys Pro Glu Ser Arg Asp Leu Leu Glu Ser Ile Cys Asn<br>              555              560              565 | | 4254 |
| agg gaa aaa gtt tca atg gct gtt att gga act atc agt gga gat gga<br>Arg Glu Lys Val Ser Met Ala Val Ile Gly Thr Ile Ser Gly Asp Gly<br>570              575              580              585 | | 4302 |
| cgt gtt gtt tta gtt gac agt gta gca gct cag aag tct att tca aat<br>Arg Val Val Leu Val Asp Ser Val Ala Ala Gln Lys Ser Ile Ser Asn<br>              590              595              600 | | 4350 |
| gga ctc cct cca cct ccc cct gct gtg gat ctt gaa ctg gag aaa gtc<br>Gly Leu Pro Pro Pro Pro Pro Ala Val Asp Leu Glu Leu Glu Lys Val<br>              605              610              615 | | 4398 |

Figure 1A Cont.- FGAM1

```
ctt ggt gac atg cct aag aaa act ttt aag ttt aat cgg gtt gtt tat    4446
Leu Gly Asp Met Pro Lys Lys Thr Phe Lys Phe Asn Arg Val Val Tyr
        620             625             630 gag cgg gag cca ctt gat att gtc cct ggg att gaa gtg ata gat tct    4494
Glu Arg Glu Pro Leu Asp Ile Val Pro Gly Ile Glu Val Ile Asp Ser
    635             640             645 ctg aag agg gta ttg agt tta ccg tct gtt tgt tca aag cgc ttc ttg    4542
Leu Lys Arg Val Leu Ser Leu Pro Ser Val Cys Ser Lys Arg Phe Leu
650             655             660             665 aca aca aaa gtt gac agg tgt gtt act ggt cta gtg gca caa cag caa    4590
Thr Thr Lys Val Asp Arg Cys Val Thr Gly Leu Val Ala Gln Gln Gln
            670             675             680 act gtt ggc cct ttg cag att ccc att gct gat gtt gct gtt aca gct    4638
Thr Val Gly Pro Leu Gln Ile Pro Ile Ala Asp Val Ala Val Thr Ala
        685             690             695 caa act ttt gct gat gtg act gga ggt gct tgt gcc att gga gaa caa    4686
Gln Thr Phe Ala Asp Val Thr Gly Gly Ala Cys Ala Ile Gly Glu Gln
        700             705             710 cca atc aaa ggt ttg tta gac ccc aaa gca atg gct cgg ttg gct gtt    4734
Pro Ile Lys Gly Leu Leu Asp Pro Lys Ala Met Ala Arg Leu Ala Val
    715             720             725 gga gaa gca cta aca aat ctt gta tgg gcg aag gtc act tcc ctt tct    4782
Gly Glu Ala Leu Thr Asn Leu Val Trp Ala Lys Val Thr Ser Leu Ser
730             735             740             745 gat gtc aag gct agt ggt aac tgg atg tat gct gcc aag ctt gat ggg    4830
Asp Val Lys Ala Ser Gly Asn Trp Met Tyr Ala Ala Lys Leu Asp Gly
            750             755             760 gaa gga gct gac atg tat gat gct gct ata tct cta tct gaa gca atg    4878
Glu Gly Ala Asp Met Tyr Asp Ala Ala Ile Ser Leu Ser Glu Ala Met
        765             770             775 att gaa ctt ggc att gct att gat gga ggg aaa gac agt ctt tct atg    4926
Ile Glu Leu Gly Ile Ala Ile Asp Gly Gly Lys Asp Ser Leu Ser Met
        780             785             790 gca gcc cac gcc gag agt gaa gtt gtc aag gct ccg gga aat ctt gtc    4974
Ala Ala His Ala Glu Ser Glu Val Val Lys Ala Pro Gly Asn Leu Val
    795             800             805 atc agt gtt tat gtt act tgt cct gat ata aca aaa aca gtg acg cca    5022
Ile Ser Val Tyr Val Thr Cys Pro Asp Ile Thr Lys Thr Val Thr Pro
810             815             820             825 gat tta aaa ctc aag gat gat ggt att ttg ctt cat att gat ttg tca    5070
Asp Leu Lys Leu Lys Asp Asp Gly Ile Leu Leu His Ile Asp Leu Ser
            830             835             840 aaa ggt aag agg cgg tta ggt gga tct gct ctt gcc cag gca ttt gac    5118
Lys Gly Lys Arg Arg Leu Gly Gly Ser Ala Leu Ala Gln Ala Phe Asp
        845             850             855
```

Figure 1A Cont.- FGAM1

```
caa gtt ggg aat gag tgt cct gat ctt gat gat gtt cct tac ctt aaa      5166
Gln Val Gly Asn Glu Cys Pro Asp Leu Asp Asp Val Pro Tyr Leu Lys
        860                 865                 870 aag gtc ttt gaa ggt gtt caa gac ctt ctt tct gat gaa ctg ata tct      5214
Lys Val Phe Glu Gly Val Gln Asp Leu Leu Ser Asp Glu Leu Ile Ser
        875                 880                 885 gct ggt cat gac atc agt gat ggt ggg ctg cta gtt tgt gcc tta gag      5262
Ala Gly His Asp Ile Ser Asp Gly Gly Leu Leu Val Cys Ala Leu Glu
890                 895                 900                 905 atg gca ttt gct ggt aat tgt gga ctt agt ttg gac ttt gca tcg caa      5310
Met Ala Phe Ala Gly Asn Cys Gly Leu Ser Leu Asp Phe Ala Ser Gln
                910                 915                 920 ggt aac agc ctt ttc caa aca ctc tat gct gaa gag ctt ggg tta gtt      5358
Gly Asn Ser Leu Phe Gln Thr Leu Tyr Ala Glu Glu Leu Gly Leu Val
            925                 930                 935 ctt gag gta agc aag aaa aat ctg gct ttg gta gtg aat aaa ttg agc      5406
Leu Glu Val Ser Lys Lys Asn Leu Ala Leu Val Val Asn Lys Leu Ser
            940                 945                 950 aat gtg gga gtt tct gct gaa atc ata ggt caa gta aca gcc aat cca      5454
Asn Val Gly Val Ser Ala Glu Ile Ile Gly Gln Val Thr Ala Asn Pro
        955                 960                 965 tca ata gaa gtt aag gtt gat ggg gag act tat tta act gaa aaa act     5502
Ser Ile Glu Val Lys Val Asp Gly Glu Thr Tyr Leu Thr Glu Lys Thr
970                 975                 980                 985 agt atc ctt agg gac atg tgg gaa gag acc agt ttt cag ctg gaa    aag   5550
Ser Ile Leu Arg Asp Met Trp Glu Glu Thr Ser Phe Gln Leu Glu    Lys
                990                 995                 1000 ttc caa agg ttg  gca tct tgt gtg gat  atg gag aaa gaa gga   cta     5595
Phe Gln Arg Leu  Ala Ser Cys Val Asp  Met Glu Lys Glu Gly   Leu
             1005              1010                   1015 aaa cat cgt tat  gaa ccc tca tgg gaa  ctg cct ttt act cct  tcc      5640
Lys His Arg Tyr  Glu Pro Ser Trp Glu  Leu Pro Phe Thr Pro  Ser
             1020              1025                  1030 ttc act gat gaa  aag ctt tat gtc tgc  aac tat aaa acc taa ag       5684
Phe Thr Asp Glu  Lys Leu Tyr Val Cys  Asn Tyr Lys Thr
             1035              1040
```

Figure 1A Cont.- FGAM1

```
ctcgagtgca ctttataaga atgtgtcagg tggattaaca attttgatag gatgtgataa      60
aaacagtctc attttaataa aacattttaa ataatatcat tttataatt atttctaatt      120
ttggctcaaa tttatcaacc agttcaagaa gatcgtgaga ttttcatata tctattttat    180
ttcaatattt aaattgaaac tttcagttga ttttttttt gtcattcatt ttgtaatcaa     240
taaaattctt tgaatttgtt gagattgatt tctcttataa tatgatgaca ttatatttaa   300
tttttcttaa ttacaggttt ttcaataaca aaattggatt gttccttaaa aaattgaatt   360
gaaaaaaaaa tgttgtcaca tagtaacttt tttttgaaa atgtcgtata gtaacttgca    420
ctttacaaat caaggacata aattaatttt agcataagtt tggctatgca tttttaaaaa   480
atagatcaac gtctaatgca aaagccactc ccgcaactca caagtttctg aatcttttgg  540
gaatttaatg tgaaaatgag agaatcaacc gataagaatt ttttatatat atttcaatta  600
agatgtgaag attattattg aagtagacac atgataagat agaaaatata cttataaaag  660
aaaataaata atatgcagat gaattatctc actcaagtaa aaatctaaac ttattatata  720
agaatgaatt ttatatttta tgtagctata gaagataatt tatcttgaga tattttaatt   780
cattaattat taatttaacg atttcaactt tttataaacc acaggcaatt tgatagagac   840
gttaaaactt taaaagaaa atccaaattg tacttacggt tcccacaggc ccaattctac    900
ctagagttta ttgaagagcc aattctattt tgttttcctc ccataaaatc aaatacacct  960
tttttgataa aagtttttt tttatctag attacataag agataatctc ttttgatttt    1020
tttatagaga aatatctttc gaattaaata tctaaaagtc acttttact gcatttaaaa   1080
gtcatataat gcactaaata ttatatataa ttaaaggata tcttgctttt atcttatttt  1140
atcatattct ttgtcaaatt ctctcttatt aaacaaaatt ttaataataa tttgggaata  1200
aataataata taattttaa cacaagacta attttatgat cttatattaa tacaagttaa   1260
ctatagttga aaatgctttt tttttttta cggaatactt gaaaatactt cttaaaataa  1320
taagtaggaa tatatcgtgt aaatttgttt aaatttattc tataaaaaat acttattta    1380
ataaaataaa caattttttt ttcttttta gtgtttgttt aaatcgtttt tacctatttt  1440
attttcttg ttttaaaaaa aatcttatct atttatgtaa aaagcattta aaaaacactt   1500
actttaaatt aaaaaatatt aatactagct tttagttttt tttttataa gatatcttac   1560
caatttacag cttcgagttt cacaagaaa ctagtgtgtt tatactgaca aagctcttat   1620
cggcgtctgt tatgaacttt ggataacgca tccgattcgg attcggctaa aagtaagcat  1680
cagcagacaa agaaattgtc gataaaacag aggaaggaga attaaaatat ataaagtagc  1740
gccaacgcaa ccaatagttg aattgaaagg ttgaaaactt tttatatttt attggtttga  1800
ttggaacttg gaagggaaag aaagagagta ccaagtggct agtagggttt tattttgtgc  1860
```

Figure 1B- FGAM2

```
cacaccaaaa ccctctcttc gttttacgcc actgccacac tctgttttgt tctggtattc   1920
ttcgattcta cttcttcttc ttgattctca ctatactcat tgtgccacag ttctgattgt   1980
gcttagtgat tctttctcaa gcttttttt tttttttttt aatttattta gagctttccc   2040
tacacttgtt cgaggacatg gcggctgcga cggaatttgg ggtgtcgcaa ttcttgcagg   2100
tttgatttta atccctctct ttgaattaac atcatatgct gctgcacccc ttttattaat   2160
ttattaattg ctgctcttgt tgggggaaaa agtttcatgc tttgatgctg tttggttttg   2220
tgattttggt ttcaggtacc tccaggcaaa ctctgttttt gaagaagaag ccacagagac   2280
agagaagaag catgttttgg ggtgcgctct ggaataggaa ttgggctctg ggatcaactc   2340
acagagcttt gcctttaagg tgccaggctc aggaaaatcc cagagctgta gtttctggtg   2400
gcgtgagcag ttctgtagag gagcaacctg ccttggttga gaagcccgct tccgaagttg   2460
ttcatttgta tcgtgtcccg ttt atg caa gca agt gca gct gct gag ctt ttg   2513
               Met Gln Ala Ser Ala Ala Ala Glu Leu Leu
                 1               5                  10 aag gaa gct caa gtg aaa atc tcc ggt cag atc gtg gaa ata cag act   2561
Lys Glu Ala Gln Val Lys Ile Ser Gly Gln Ile Val Glu Ile Gln Thr
             15                  20                  25 gag cag tgt tat aat gtt ggc ctt agt tca caa ctt tct ggt gga aaa   2609
Glu Gln Cys Tyr Asn Val Gly Leu Ser Ser Gln Leu Ser Gly Gly Lys
             30                  35                  40 ttt tcg gtc ctt aga tgg ctt ctt caa gaa aca ttt gag cct gag aat   2657
Phe Ser Val Leu Arg Trp Leu Leu Gln Glu Thr Phe Glu Pro Glu Asn
             45                  50                  55 ctg gga act gag agc ttt ctt gag aag aag aag aaa gag ggt ctg agt   2705
Leu Gly Thr Glu Ser Phe Leu Glu Lys Lys Lys Lys Glu Gly Leu Ser
 60                  65                  70 cca gtt att gtt gaa gtt ggc ccc agg ctg tca ttt acc acg gca tgg   2753
Pro Val Ile Val Glu Val Gly Pro Arg Leu Ser Phe Thr Thr Ala Trp
 75                  80                  85                  90 tct acc aat gct gtt gca att tgc caa gcc tgt ggt ttg aca gaa gtg   2801
Ser Thr Asn Ala Val Ala Ile Cys Gln Ala Cys Gly Leu Thr Glu Val
                 95                 100                 105 aac cgt ttg gaa cgg tcc agg agg tac ttg ttg ttc acc acc act gaa   2849
Asn Arg Leu Glu Arg Ser Arg Arg Tyr Leu Leu Phe Thr Thr Thr Glu
            110                 115                 120 ctg caa gat tat caa atc aat gat ttt acg tct atg gtg cat gat agg   2897
Leu Gln Asp Tyr Gln Ile Asn Asp Phe Thr Ser Met Val His Asp Arg
            125                 130                 135 atg act gaa tgt gtt tat gtt cag aag cta aca tcc ttc gag act agt   2945
Met Thr Glu Cys Val Tyr Val Gln Lys Leu Thr Ser Phe Glu Thr Ser
        140                 145                 150
```

Figure 1B Cont.- FGAM2

```
gtt gtt cca gag gag att cgt tat ata cct gtc atg gag aag ggg cga    2993
Val Val Pro Glu Glu Ile Arg Tyr Ile Pro Val Met Glu Lys Gly Arg
155             160             165             170 aag gca tta gaa gag att aat ctg gag atg ggt ttt gcc ttt gat gac    3041
Lys Ala Leu Glu Glu Ile Asn Leu Glu Met Gly Phe Ala Phe Asp Asp
            175             180             185 cag gat ttg gaa tac tac acc aaa ctc ttc agg gaa gac att aag cgt    3089
Gln Asp Leu Glu Tyr Tyr Thr Lys Leu Phe Arg Glu Asp Ile Lys Arg
                190             195             200 aac cca aca aat gtg gaa ttg ttt gat att gcg cag tcc aac agt gag    3137
Asn Pro Thr Asn Val Glu Leu Phe Asp Ile Ala Gln Ser Asn Ser Glu
        205             210             215 cac agc aga cac tgg ttt ttt act gga aat att ttc att gat gga cag    3185
His Ser Arg His Trp Phe Phe Thr Gly Asn Ile Phe Ile Asp Gly Gln
        220             225             230 cct gtg aat aga act ctc atg cag att gtg aaa agt act ctg cag gca    3233
Pro Val Asn Arg Thr Leu Met Gln Ile Val Lys Ser Thr Leu Gln Ala
235             240             245             250 aac cca aat aac tca gtt att ggc ttc aag gat aac tcg agt gca atg    3281
Asn Pro Asn Asn Ser Val Ile Gly Phe Lys Asp Asn Ser Ser Ala Met
            255             260             265 cag ggg ttt tcc agt gaa gca gct ccg acc agt tca acc tgg ttc aac    3329
Gln Gly Phe Ser Ser Glu Ala Ala Pro Thr Ser Ser Thr Trp Phe Asn
            270             275             280 ttg tcc att aga agt tgc agt cat gag tta gat atc ttg ttt aca gcc    3377
Leu Ser Ile Arg Ser Cys Ser His Glu Leu Asp Ile Leu Phe Thr Ala
            285             290             295 gaa aca cat aat ttt cca tgt gca gtg gca cct tat cct ggt gca gag    3425
Glu Thr His Asn Phe Pro Cys Ala Val Ala Pro Tyr Pro Gly Ala Glu
        300             305             310 aca ggt gca gga ggt cgt att agg gat aca cat gct aca gga agg ggg    3473
Thr Gly Ala Gly Gly Arg Ile Arg Asp Thr His Ala Thr Gly Arg Gly
315             320             325             330 tcc ttt gtc caa gca gct aca gct ggt tat tgc gtt ggg aat ctc aac    3521
Ser Phe Val Gln Ala Ala Thr Ala Gly Tyr Cys Val Gly Asn Leu Asn
            335             340             345 aca cca ggc ttt tat gct cca tgg gaa gat tcc tcc ttt act tat cca    3569
Thr Pro Gly Phe Tyr Ala Pro Trp Glu Asp Ser Ser Phe Thr Tyr Pro
        350             355             360 tca aat ttg gca cca cct tta cag att ctg ata gat tct agt aat ggt    3617
Ser Asn Leu Ala Pro Pro Leu Gln Ile Leu Ile Asp Ser Ser Asn Gly
            365             370             375 gca tct gac tat ggg aac aaa ttt gga gag cca tga tca ggt ttc       3665
Ala Ser Asp Tyr Gly Asn Lys Phe Gly Glu Pro Leu Ile Gln Gly Phe
        380             385             390
```

Figure 1B Cont.- FGAM2

```
tgt aga act ttt gga atg aga ctt ccc agt ggg gag agg cga gaa tgg      3713
Cys Arg Thr Phe Gly Met Arg Leu Pro Ser Gly Glu Arg Arg Glu Trp
395             400             405             410 ttg aag cct atc atg ttc agc gca ggc att gga cag att gac cac ctt      3761
Leu Lys Pro Ile Met Phe Ser Ala Gly Ile Gly Gln Ile Asp His Leu
                415             420             425 cat ata tca aag gga gag cct gac att ggg atg ctg gtt gtt aag att      3809
His Ile Ser Lys Gly Glu Pro Asp Ile Gly Met Leu Val Val Lys Ile
            430             435             440 gga ggc ccg gct tat cgt att ggt atg gga ggc ggg gca gcc tca agc      3857
Gly Gly Pro Ala Tyr Arg Ile Gly Met Gly Gly Gly Ala Ala Ser Ser
        445             450             455 atg gtc agt ggg cag aat gat gca gag ctt gat ttc aat gct gtg caa      3905
Met Val Ser Gly Gln Asn Asp Ala Glu Leu Asp Phe Asn Ala Val Gln
    460             465             470 cgt ggg gat gct gag atg gct caa aaa cta tat cgt ctt gtg cgt gct      3953
Arg Gly Asp Ala Glu Met Ala Gln Lys Leu Tyr Arg Leu Val Arg Ala
475             480             485             490 tgt att gag atg ggg gat aaa aac cca att atc agc att cat gat cag      4001
Cys Ile Glu Met Gly Asp Lys Asn Pro Ile Ile Ser Ile His Asp Gln
                495             500             505 gga gct ggt ggg aat tgc aat gtt gta aag gaa att ata tat cca aag      4049
Gly Ala Gly Gly Asn Cys Asn Val Val Lys Glu Ile Ile Tyr Pro Lys
            510             515             520 ggt gct gag ata gat gtt cga gca att gtg gtt ggc gat cat aca atg      4097
Gly Ala Glu Ile Asp Val Arg Ala Ile Val Val Gly Asp His Thr Met
        525             530             535 tct gtt cta gaa att tgg ggt gca gag tat cag gag cag gat gca atc      4145
Ser Val Leu Glu Ile Trp Gly Ala Glu Tyr Gln Glu Gln Asp Ala Ile
    540             545             550 ttg gtg aag cct gaa agt cgt gat ctt ctg gaa tca atc tgt aac agg      4193
Leu Val Lys Pro Glu Ser Arg Asp Leu Leu Glu Ser Ile Cys Asn Arg
555             560             565             570 gag aaa gtt tca atg gct gtt att gga act atc agt ggt gat gga cgt      4241
Glu Lys Val Ser Met Ala Val Ile Gly Thr Ile Ser Gly Asp Gly Arg
                575             580             585 gtt gtt tta gtt gac agt gta gca gtc cag aag tct att tca aat gga      4289
Val Val Leu Val Asp Ser Val Ala Val Gln Lys Ser Ile Ser Asn Gly
            590             595             600 ctc act tca cct ccc cct gcc gtg gat ctt gaa ttg gag aaa gtc ctt      4337
Leu Thr Ser Pro Pro Pro Ala Val Asp Leu Glu Leu Glu Lys Val Leu
        605             610             615 ggt gac atg cct aag aaa act ttt aaa ttt aat cgg gtt gtt tat gag      4385
Gly Asp Met Pro Lys Lys Thr Phe Lys Phe Asn Arg Val Val Tyr Glu
    620             625             630
```

Figure 1B Cont.- FGAM2

```
agg gag cca ctt gat att gcc cct ggg att gaa gtg ata gat tcc cta    4433
Arg Glu Pro Leu Asp Ile Ala Pro Gly Ile Glu Val Ile Asp Ser Leu
635                 640                 645                 650 aag agg gta ttg agt tta ccg tct gtt tgt tca aag cgc ttc tta aca    4481
Lys Arg Val Leu Ser Leu Pro Ser Val Cys Ser Lys Arg Phe Leu Thr
                    655                 660                 665 aca aaa gtt gat agg tgt gtt act ggt cta gtg gca caa caa caa act    4529
Thr Lys Val Asp Arg Cys Val Thr Gly Leu Val Ala Gln Gln Gln Thr
                670                 675                 680 gtt ggc cct ttg cag att ccc att gct gat gtt gct gtt aca gct caa    4577
Val Gly Pro Leu Gln Ile Pro Ile Ala Asp Val Ala Val Thr Ala Gln
            685                 690                 695 act ttt gtt gat gtg act gga ggt gct tgt gcc att ggt gag caa ccc    4625
Thr Phe Val Asp Val Thr Gly Gly Ala Cys Ala Ile Gly Glu Gln Pro
700                 705                 710 atc aaa ggc ctg tta gac ccc aaa gca atg gct cgg ttg gct gtt gga    4673
Ile Lys Gly Leu Leu Asp Pro Lys Ala Met Ala Arg Leu Ala Val Gly
715                 720                 725                 730 gaa gca cta aca aat ctt gta tgg gca aag gtc act tcc ctt tct gat    4721
Glu Ala Leu Thr Asn Leu Val Trp Ala Lys Val Thr Ser Leu Ser Asp
                735                 740                 745 gtc aag gct agt ggt aac tgg atg tat gct gcc aag ctt gat ggg gaa    4769
Val Lys Ala Ser Gly Asn Trp Met Tyr Ala Ala Lys Leu Asp Gly Glu
            750                 755                 760 gga gct gac atg tat gat gca gct ata tct cta tct gaa gca atg att    4817
Gly Ala Asp Met Tyr Asp Ala Ala Ile Ser Leu Ser Glu Ala Met Ile
        765                 770                 775 gaa ctt ggc att gct att gat gga ggg aaa gac agc ctt tct atg gca    4865
Glu Leu Gly Ile Ala Ile Asp Gly Gly Lys Asp Ser Leu Ser Met Ala
    780                 785                 790 gcc cac gct gaa agt gaa gtt gtc aag gca cca ggr aat ctt gtc atc    4913
Ala His Ala Glu Ser Glu Val Val Lys Ala Pro Xaa Asn Leu Val Ile
795                 800                 805                 810 agt gtk tat gtt act tgt cct gat ata aca aaa aca gtg act cca gat    4961
Ser Xaa Tyr Val Thr Cys Pro Asp Ile Thr Lys Thr Val Thr Pro Asp
                815                 820                 825 tta aaa ctc aag gat gat ggt att ttg ctt cat att gat ttg tca aaa    5009
Leu Lys Leu Lys Asp Asp Gly Ile Leu Leu His Ile Asp Leu Ser Lys
            830                 835                 840 ggt aag agg cgg tta ggt gga tct gct ctt gcc cag gcg ttt gac caa    5057
Gly Lys Arg Arg Leu Gly Gly Ser Ala Leu Ala Gln Ala Phe Asp Gln
        845                 850                 855 gtt gga gat gag tgt cct gat cct gat gat gtt cct tac ctt aaa aag    5105
Val Gly Asp Glu Cys Pro Asp Pro Asp Asp Val Pro Tyr Leu Lys Lys
    860                 865                 870
```

Figure 1B Cont.- FGAM2

```
gcc ttt gaa ggt gtt caa gac ctt ctt tct gat gaa ttg ata tct gct    5153
Ala Phe Glu Gly Val Gln Asp Leu Leu Ser Asp Glu Leu Ile Ser Ala
875             880             885             890 ggt cat gac atc agt gat ggt ggg ctg cta gtt tgt gcc tta gag atg    5201
Gly His Asp Ile Ser Asp Gly Gly Leu Leu Val Cys Ala Leu Glu Met
                895             900             905 gca ttt gct ggt aac tgt ggt ctt agt ttg gac ttg gcg tcg caa ggt    5249
Ala Phe Ala Gly Asn Cys Gly Leu Ser Leu Asp Leu Ala Ser Gln Gly
                910             915             920 acc agc ctt ttc caa aca ctc tat gct gaa gag ctt ggg tta gtt ctt    5297
Thr Ser Leu Phe Gln Thr Leu Tyr Ala Glu Glu Leu Gly Leu Val Leu
        925             930             935 gag gta aac aag aaa aat ctg gct ttg gta atg gat aaa ttg agt aat    5345
Glu Val Asn Lys Lys Asn Leu Ala Leu Val Met Asp Lys Leu Ser Asn
        940             945             950 gtg gga gtt tca gct gaa atc att ggt caa gta aca gcc aat cca tca    5393
Val Gly Val Ser Ala Glu Ile Ile Gly Gln Val Thr Ala Asn Pro Ser
955             960             965             970 ata gaa gtt aag gtt gat ggg gag act tat tta act gaa aaa act agt    5441
Ile Glu Val Lys Val Asp Gly Glu Thr Tyr Leu Thr Glu Lys Thr Ser
                975             980             985 atc ctt agg gac ttg tgg gaa gag acc agt ttt cag ctg gaa  aag ttc   5489
Ile Leu Arg Asp Leu Trp Glu Glu Thr Ser Phe Gln Leu Glu  Lys Phe
                990             995              1000 caa aga ttg  gca tcc tgt gtg gat  atg gag aaa gaa gga  ctt aaa     5534
Gln Arg Leu  Ala Ser Cys Val Asp  Met Glu Lys Glu Gly  Leu Lys
             1005            1010             1015 cat cga tat  gag ccc tca tgg gaa  ctg cct ttt act ccc  acc ttc     5579
His Arg Tyr  Glu Pro Ser Trp Glu  Leu Pro Phe Thr Pro  Thr Phe
             1020            1025             1030 act gat gga  aag ctt ctg tct gca  act ata aaa cct aaa  gtg gct     5624
Thr Asp Gly  Lys Leu Leu Ser Ala  Thr Ile Lys Pro Lys  Val Ala
             1035            1040             1045 gtg att aga  gaa gaa ggc agt aat  gga gac aga gaa atg  gct gca     5669
Val Ile Arg  Glu Glu Gly Ser Asn  Gly Asp Arg Glu Met  Ala Ala
             1050            1055             1060 gca ttt tat  gct gct ggt ttt gaa  cca tgg gat att act  atg tca     5714
Ala Phe Tyr  Ala Ala Gly Phe Glu  Pro Trp Asp Ile Thr  Met Ser
             1065            1070             1075 gac ctt ctt  aat gga aag atc tct  ttg caa gac ttc cgc  gga att     5759
Asp Leu Leu  Asn Gly Lys Ile Ser  Leu Gln Asp Phe Arg  Gly Ile
             1080            1085             1090 gtg ttt gtt  ggt gga ttt agc tat  gct gat gtg ctt gat  tct gca     5804
Val Phe Val  Gly Gly Phe Ser Tyr  Ala Asp Val Leu Asp  Ser Ala
             1095            1100             1105
```

Figure 1B Cont.- FGAM2

```
aaa ggt tgg tct gct agc ata aga ttc aat gag tcc gtt tta caa      5849
Lys Gly Trp Ser Ala Ser Ile Arg Phe Asn Glu Ser Val Leu Gln
        1110                1115                1120 caa ttt cag gag ttt tac aag cgt cca gac act ttc agt ctc ggt      5894
Gln Phe Gln Glu Phe Tyr Lys Arg Pro Asp Thr Phe Ser Leu Gly
        1125                1130                1135 gta tgc aat gga tgt cag cta atg gct ttg ttg gga tgg gta ccg      5939
Val Cys Asn Gly Cys Gln Leu Met Ala Leu Leu Gly Trp Val Pro
        1140                1145                1150 ggt cca caa gtt ggg ggt gtg cat ggt gct ggt ggc gac cta tca      5984
Gly Pro Gln Val Gly Gly Val His Gly Ala Gly Gly Asp Leu Ser
        1155                1160                1165 caa ccg agg ttc att cat aat gag tca ggg cgg ttt gag tgc cgc      6029
Gln Pro Arg Phe Ile His Asn Glu Ser Gly Arg Phe Glu Cys Arg
        1170                1175                1180 ttt aca agt gtg acc ata aag gac tca ccg gct ata atg ttc aaa      6074
Phe Thr Ser Val Thr Ile Lys Asp Ser Pro Ala Ile Met Phe Lys
        1185                1190                1195 gac atg gca ggt agc aca ttg ggt ata tgg gct gct cat ggt gag      6119
Asp Met Ala Gly Ser Thr Leu Gly Ile Trp Ala Ala His Gly Glu
        1200                1205                1210 gga aga gct tat ttc cca gat gaa ggc gtg ttg gac cgt ata gtt      6164
Gly Arg Ala Tyr Phe Pro Asp Glu Gly Val Leu Asp Arg Ile Val
        1215                1220                1225 cat tct gag ttg gct cct ata aga tac tgt gat gat gct ggg aat      6209
His Ser Glu Leu Ala Pro Ile Arg Tyr Cys Asp Asp Ala Gly Asn
        1230                1235                1240 cca aca gag gcc tac cct ttc aat gtg aat ggc tct cct tta ggg      6254
Pro Thr Glu Ala Tyr Pro Phe Asn Val Asn Gly Ser Pro Leu Gly
        1245                1250                1255 gtg gca gct att tgt tcc cca gat ggg agg cat ctt gcc atg atg      6299
Val Ala Ala Ile Cys Ser Pro Asp Gly Arg His Leu Ala Met Met
        1260                1265                1270 cct cat cct gag cgt tgc ttc tta atg tgg cag ttc cca tgg tat      6344
Pro His Pro Glu Arg Cys Phe Leu Met Trp Gln Phe Pro Trp Tyr
        1275                1280                1285 cca aag cag tgg gat gtg gag aag aag ggg cct agt cct tgg tta      6389
Pro Lys Gln Trp Asp Val Glu Lys Lys Gly Pro Ser Pro Trp Leu
        1290                1295                1300 cgc atg ttc cag aat gca aga gag tgg tgt tcc tga aatgatcaaa       6435
Arg Met Phe Gln Asn Ala Arg Glu Trp Cys Ser
        1305                1310
```

Figure 1B Cont.- FGAM2

Fig. 2A

|  |  |  | Seq ID Nos. |
|---|---|---|---|
| | | ATP Binding | |
| FGAM1 | 309 | PYPGAETGAGGRIRDTHATGRGSFVQAATAGYCVGNLNTPGFYAPWEDPSFTYPSNLAPP | 2 |
| FGAM2 | 309 | PYPGAETGAGGRIRDTHATGRGSFVQAATAGYCVGNLNTPGFYAPWEDSSFTYPSNLAPP | 4 |
| DM-FGAM | | PFSGATTGTGGRLRDVQGVGRGGVPIAGTAGYCVGALHIPGYKQPYEPLDFKYPATFAPP | 5 |
| HUMAN-FGAM | | PFSGATTGTGGRIRDVQCTGRGAHVVAGTAGYCFGNLHIPGYNLPWEDLSFQYPGNFARP | 6 |
| ECOLI-FGAM | | PWPGAATGSGGEIRDEGATGRGAKPKAGLVGFSVSNLRIPGFEQPWEE-DFGKPERIVTA | 7 |
| | | Gln Binding | |
| FGAM1 | 1051 | EEGSNGDREMAAAFYAAGFEPWDITMSDLLNGKISLLDFRGIVFVGGFSYADVLDSAKGW | 2 |
| FGAM2 | 1051 | EEGSNGDREMAAAFYAAGFEPWDITMSDLLNGKISLQDFRGIVFVGGFSYADVLDSAKGW | 4 |
| DM-FGAM | | EEGVNSEREMMACLLRANFEVHDVTMSDLLQGTASVSQYRGLIFPGGFSYADTLGSAKGW | 8 |
| HUMAN-FGAM | | EEGSNGDREMADAFHLAGFEVWDVTMQDLCSGAIGLDTFRGVAFVGGFSYADVLGSAKGW | 9 |
| ECOLI-FGAM | | EQGVNSHVEMAAAFHRAGFDAIDVHMSDLLTGRTGLEDFHALVACGGFSYGDVLGAGEGW | 10 |
| | | Gln Binding | |
| FGAM1 | 1111 | SASIRFNESVLQQFQEFYKRPDTFSLGVCNGCQLMALLGWVPGPQVGGVHGAGG----DL | 2 |
| FGAM2 | 1111 | SASIRFNESVLQQFQEFYKRPDTFSLGVCNGCQLMALLGWVPGPQVGGVHGAGG----DL | 4 |
| DM-FGAM | | AANILHNPRLLPQFEAFKRRQDVFSLGICNGCQLMTLIGFVGSAKSEVGADP-------- | 11 |
| HUMAN-FGAM | | AAAVTFHPRAGAELRRFRKRPDTFSLGVCNGCQLLALLGWVGGDPNEDAAEMGPDSQPAR | 12 |
| ECOLI-FGAM | | AKSILFNDRVRDEFATFFHRPQTLALGVCNGCQMMSNLRELIPGSE---------L--W | 13 |
| | | Gln Binding | |
| FGAM1 | 1227 | VHSELAPIRYCDDAGNPTEAYPFNANGSPLGVAAICSPDGRHLAMMPHPERCFLMWQFPW | 2 |
| FGAM2 | 1227 | VHSELAPIRYCDDAGNPTEAYPFNVNGSPLGVAAICSPDGRHLAMMPHPERCFLMWQFPW | 4 |
| DM-FGAM | | QSEQLVTLQYVDDVGKPTELYPLNPNGSPQGIAGLCSSDGRHLALMPHPERCSSMYQWPY | 14 |
| HUMAN-FGAM | | EARGLAPLHWADDDGNPTEQYPLNPNGSPGGVAGICSCDGRHLAVMPHPERAVRPWQWAW | 15 |
| ECOLI-FGAM | | ESKGLVALRYVDNFGKVTETYPANPNGSPNGITAVTTESGRVTIMMPHPERVFRTVSNSW | 16 |

Figure 2B

*FGAM1* promoter alignment to *wun1* promoter

Percent Similarity: 94.595   Percent Identity: 94.595

|  | Nt. no. | | | Seq ID Nos. |
|---|---|---|---|---|
| FGAM1 | 795 | AACCGATATATATATATATATATATATATATATCAAT | 831 | 1 |
|  |  | \|\|\|\|\|\|\|\|\|\|\|\|\|\|\|\|\|\|\|\|\|\|\|\|\|\|\|\|\|\|\|\| \|\| | | |
| Wun1 |  | aaccgatatatatatatatatatatatatatatat | | 17 |

*FGAM2* promoter alignment to *wun1* promoter

Percent Similarity: 68.354   Percent Identity: 68.354

|  | Nt. no. | | | Seq ID Nos. |
|---|---|---|---|---|
| FGAM2 | 1332 | ATATCGTGTAAATTTGTTTAAATTTATTCTATAAAAAATACTTATTTTAA | 1381 | 3 |
|  |  | \|\|\|\|\|\|\|  \|\|\|\|  \|  \|\|  \|  \|\|  \|    \|  \|  \|  \|\|\|   \|\|    \|\|\|\| | | |
| Wun1 |  | atatcgttaaaatattttaatatcttgttgaaatataattttttatttag | | 18 |
|  | 1382 | TAAAATAA....ACAATTTTTTTTCTTTTTTA | 1410 | 3 |
|  |  | \|\|\|\|\|\|\|\|    \|  \|\|\|\|  \|\|\|\|\|  \|\|  \|\|  \| | | |
|  |  | taaaataatatgagaattaattttttttattaa | | 18 |

SOYBEAN FGAM SYNTHASE PROMOTERS USEFUL IN NEMATODE CONTROL

GOVERNMENT INTEREST

The U.S. Government may have certain rights in this invention pursuant to United States Department of Agriculture Grant No. 96-35302-3385.

RELATEDNESS OF THE APPLICATION

The subject application claims the benefit of priority from U.S. Ser. No. 60/556,745, filed Mar. 26, 2004, which is incorporated herein in its entirety.

REFERENCE TO SEQUENCE LISTING

The present application incorporates by reference a file named:1231–221 Sequence Listing. ST25. txt including SEQ ID NO: 1 to SEQ ID NO: 20, provided in a computer readable form and paper copy. The sequence listing information recorded on the computer readable form is identical to the paper copy sequence listing.

FIELD OF THE INVENTION

The subject invention relates to nematode responsive domains from the soybean FGAM synthase gene, which can be useful in reducing parasite infection or infestation.

BACKGROUND OF THE INVENTION

The soybean cyst nematode (SCN) *Heterodera glycines* Ichinohe is considered the most economically debilitating disease-causing pathogen to affect soybean cultivation (Noel, G. R. (1992) in Riggs, R. D., Wrather, J. A. (eds) Biology and management of the soybean cyst nematode, APS Press, St. Paul, Minn., pp 8–10), causing losses of up to one billion dollars annually (Kim, D. G. et al. (1997) J. Nematol. 29:173–179). Several Hg types of SCN (Nieblack, T. L. et al. (2002) J. Nematol. 34:279–288) exist in the field (Riggs, R. D. et al. (1988) J. Nematol. 23:149–154) and several soybean genes that confer resistance have been identified. The most important of these genes have been mapped to linkage groups G and A2 of the soybean genetic map (Webb, D. M. et al (1995) Theor. Appl. Genet. 85:136–138; Concibido, V. C. et al. (1996) Theor. Appl. Genet. 93:234–241; and Meksem, K. et al. (2001) Theor. Appl. Genet. 103:710–718).

Several approaches have been undertaken to characterize nematode-responsive gene expression patterns within feeding sites of the soybean root. Changes in mRNA abundance were studied by in vitro translation to proteins (Hammond-Kossack, K. E. et al. (1989) Physiol. Mol. Plant Pathol. 37:339–354; Potenza, C. L. et al. (1996) J. Nematol. 28:475–484; and Oberschmidt, I. et al. (1996) Fourth annual meeting of the European union AIR-CAP on Mechanisms for resistance against plant parasitic nematodes, Toledo, Spain, p. 13). Subtractive hybridization of cDNA libraries prepared from nematode-infected and uninfected roots has yielded "infection-specific" clones. This approach has been utilized in tomato plants infected with root-knot nematodes (Van der Eycken, W. et al. (1996) Plant J. 9:45–54), and in potatoes infected with cyst nematodes (Niebel, A. et al. (1995) MPMI 8:371–378). Likewise, several PCR-based libraries have been constructed to permit the cloning of "giant cell-specific" transcripts (Wilson, M. A. et al. (1994) Phytopathol. 84:299–303; and Bird, D. M. et al. (1994) MPMI 7:419–424). Use of the differential display technique has yielded several interesting candidate genes in the *Arabidopsis-Meloidogyne* interaction (Vercauteren, I. et al. (2001) MPMI 14:288–299) and the soybean-SCN interaction (Hermsmeier, D. et al. (1998) MPMI 11:1258–1263). Promoter-GUS fusion (Opperman, C. H. et al. (1994) Science 263:221–223) and promoter trap (Barthels, N. et al. (1997) The Plant Cell 9:2119–2134; and Puzio, P. S. et al. (1998) Physiol. Mol. Plant Pathol. 53:177–193) approaches have also been implemented to identify nematode-responsive loci.

In a previous report (Vaghchhipawala, Z. E. et al. (2001) MPMI 14:42–54), we showed that several genes were up-regulated within the syncytium during colonization of the root by SCN. We determined the map locations of some of the soybean genes responsive to nematode infection by locating them on the public soybean map (Shoemaker, R. C. et al. (1996) in D. P. S. Verma and R. C. Shoemaker (eds) Biotechnology in Agriculture, No. 14, Soybean: genetics, Molecular Biology and Biotechnology, CAB International, Wallingford, Oxon, UK, pp. 37–56). A particularly interesting candidate was phosphoribosylformylglycinamidine ribonucleotide (FGAM) synthase. This gene mapped to the same 3.0-cM interval of Linkage Group G where the major soybean SCN resistance locus Rhg1 maps (Mudge, J. et al. (1997) Crop Sci. 37:1611–1615).

FGAM synthase was of interest because of its coincident location within the genomic interval containing Rhg1 and its up-regulated expression within the nematode feeding site. The enzyme FGAM synthase catalyzes the fifth step of the de novo purine biosynthetic pathway, effecting the ATP-dependent transfer of the glutamine amido group to the C-4 carbonyl of FGAR (5'-phosphoribosyl-N-formylglycinamide). To investigate this soybean gene further, we isolated and characterized two FGAM synthase loci. The two loci were highly similar in sequence. Analysis of the two copies revealed distinct functions and/or expression profiles during development and syncytium formation. As is described herein, the promoters of both FGAM synthase copies were found to contain novel nematode responsive domains that are active during syncytium formation.

SUMMARY OF THE INVENTION

The subject invention concerns the identification of soybean gene promoter sequences that contain nematode responsive domains. The nematode responsive domain is active during nematode establishment of a feeding site on the soybean, resulting in altered expression of downstream coding sequences.

As discussed herein, they soybean cyst nematode (SCN) is an economically debilitating disease-causing pathogen in soybean cultivation. Several soybean genes that confer resistance have been identified. One of the most important nematode resistance genes, rhg1, has been mapped to a distal region of MLG-G in soybean. A simplified genetic system to identify soybean genes with modified expression in response to SCN led to the identification of several genes within the nematode feeding sites (Vaghchhipawala et al. (2001) supra). The genes were mapped to reveal their linkage relationship to known QTLs associated with soybean cyst nematode (SCN) resistance. One candidate, a phosphoribosylformylglycinamidine (FGAM) synthase (EC# 6.3.5.3) gene, mapped to the same genomic interval as the major SCN resistance gene rhg1 within Linkage Group G. As is detailed herein, isolation of FGAM synthase from a soybean bacterial artificial chromosome (BAC) library revealed two highly homologous paralogs. The genes appeared to be well conserved from bacteria to humans. Promoter analysis of the two soybean homologs was carried out with the *Arabidopsis thaliana-Heterodera schachtii* system to investigate gene response to nematode feeding. As reported herein, the two promoters and their derived deletion constructions effected green fluorescent protein expression within nematode feeding sites. It was found that the 1.0-kbp promoter sequence immediately adjacent to the translation start site was sufficient to direct expression of GFP within syncytia at the feeding site. The observed expression of GFP within the feeding sites indicates that plant gene expression is redirected within feeding sites to benefit the parasitic nematode.

Thus, in one embodiment, the subject invention is a molecule that comprises a soybean promoter sequence that comprises a nematode responsive domain, i.e., a domain that is responsive to nematode establishment of a feeding site in the plant.

As is set forth in the Examples, the promoter sequence can comprise a sequence selected from the group consisting of soybean FGAM synthase Pr1-1.0 (nucleotides 1790–2483 of SEQ. ID NO. 2), Pr2-1.0 (nucleotides 1551–2547 of SEQ. ID NO. 1), Pr1-1.5 (nucleotides 1271–2483 of SEQ. ID NO. 2), Pr2-1.5 (nucleotides 991–2547 of SEQ. ID NO. 1), Pr1-2.5 (nucleotides 124–2483 of SEQ. ID NO. 2) and Pr2-2.5 (nucleotides 19-2547 of SEQ. ID NO. 1).

Further, the promoter sequence can be a sequence that has at least 50% homology with that of Pr1-1.0 or Pr2-1.0 of soybean FGAM synthase. With increasing preference, the promoter sequence has at least 60%, 70%, 80%, 90% or 95% homology to Pr1-1.0 or Pr2-1.0. To be encompassed within the scope of the subject invention, these variant promoter sequences must remain functional as nematode responsive domains.

It will be apparent that minor additions, deletions or substitutions can be made to Pr1-1.0 or Pr2-1.0, while retaining or perhaps enhancing the nematode responsive function. All of these variants are encompassed within the scope of the subject invention.

In another embodiment, the subject invention includes a molecule that is a promoter comprising the nematode responsive domain and a heterologous DNA operatively linked to the promoter. The heterologous DNA encodes a product that is disruptive of nematode attack. The disruptive product may be toxic to the plant cell or to the nematode.

The subject invention also includes a transfected plant (e.g., soybean) cell comprising the above-described molecule comprising the nematode responsive domain. It also includes transgenic plants comprising the transfected plant cells.

In another embodiment, the invention includes a method of reducing nematode infection of a plant (e.g., soybean) comprising transfecting plant cells of said plant with a vector comprising a promoter containing the nematode responsive domain and a heterologous DNA operatively linked to the promoter.

All references cited herein are incorporated in their entirety by reference.

BRIEF DESCRIPTION OF THE DRAWINGS

FIG. 1A is the nucleotide sequence and amino acid sequence for FGAM1 (SEQ. ID NOS. 1 and 2).

FIG. 1B is the nucleotide sequence and amino acid sequence for FGAM2 (SEQ. ID NOS. 3 and 4).

FIG. 2A is the sequence alignments of the soybean FGAM synthase gene with other known FGAM sequences. Multiple alignment of amino acid sequences (Higgins, D.G. et al. (1988) Gene 73:237–244) for genes FGAM1 (SEQ ID NO: 2), FGAM2 (SEQ ID NO: 4), *Drosophila melanogaster* (SEQ ID NO: 5, SEQ ID NO: 8, SEQ ID NO: 11, and SEQ ID NO: 14), *Homo sapiens* (SEQ ID NO: 6, SEQ ID NO: 9, SEQ ID NO: 12, and SEQ ID NO: 15) and *E.coli* (SEQ ID NO: 7, SEQ ID NO: 10, SEQ ID NO: 13 and SEQ ID NO: 16) using the ClustalW program are shown. Only conserved domains are shown. Identical amino acids are in bold. The ATP-binding domain and the three glutamine-binding domains are overlined.

FIG. 2B is the Bestfit analysis of the sequence homology of promoter regions of FGAM1 (SEQ ID NO: 1) and FGAM2 (SEQ ID NO: 3) genes with the wun1 promoter (SEQ ID NO: 17 and SEQ ID NO: 18) from potato (Hansen, E. et al. (1996) Physiol. Mol. Plant Pathol. 48:161–170).

DETAILED DESCRIPTION

Figure 3:
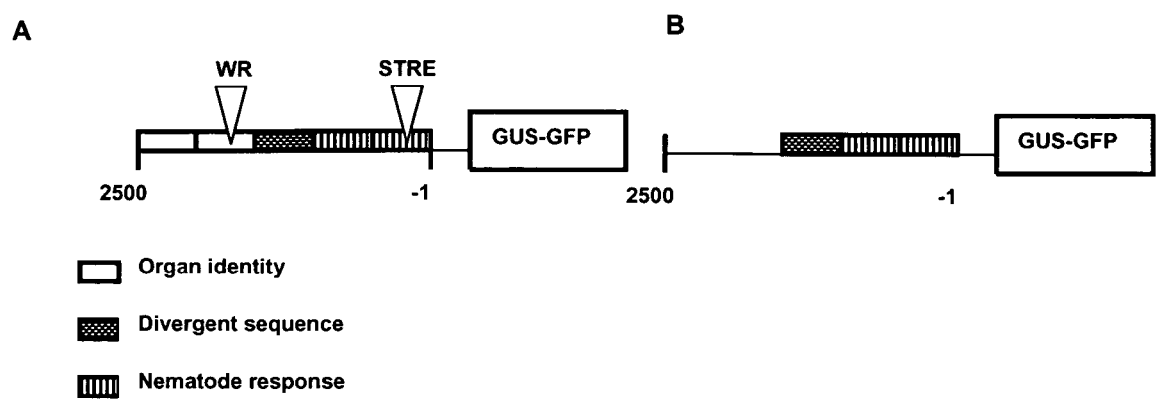
FIG. 3 is a diagrammatic representation of promoter organization for genes FGAM1 (A) and FGAM2 (B). Promoter deletions were generated from the approximately 2500 bp end using PCR. Domains identified in these promoters via functional or sequence analysis are indicated. WR indicates a wound response element identified by sequence homology and shown functionally in Pr1-2.5 plants. STRE designates a stress response element.

The subject invention concerns the identification of soybean gene promoter sequences that contain a nematode responsive domain, and the use of said domain in the control of nematode infection of soybeans.

A "nematode responsive domain" is a region of the plant (e.g., soybean) promoter that is active in a nematode established feeding site on the plant. Without wishing to be bound by a particular theory, it is believed that a nematode protein or other molecule may bind to the nematode responsive domain of the promoter to control expression of downstream coding sequences during establishment of a feeding site. A nematode responsive domain is "functional" if the mRNA expression of the downstream coding sequence is up-regulated in the feeding site syncytium by at least 10% as compared to plant cells of the same tissue type that are not nematode feeding sites. "Functional" nematode responsive domain can also mean, with increasing preference, increased expression of 20%, 30%, 40%, 50%, 60%, 70%, 80%, 90%, 100% or more. Methods for determining increase in amount of mRNA expression are known to persons skilled in the art.

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

Plant transformation involves the construction of an expression vector which will function in plant cells. Such a vector comprises a heterologous DNA under control of or operatively linked to a regulatory element (for example, a promoter). The expression vector may contain one or more such operatively linked gene/regulatory element combinations. The vector(s) may be in the form of a plasmid, and can be used alone or in combination with other plasmids, to provide transformed plants, using transformation methods as described below to incorporate heterologous sequences into the genetic material of the plant.

The heterologous DNA may encode any product that is disruptive of nematode attack when that DNA is transcribed (and if necessary, translated) in a plant cell. The product can include proteins, peptides, and non-protein products such as antisense RNAs, aptamers and the like. Atkinson, H. J. et al. (2003) Ann. Rev. Phytopathol. 41:615, review information on direct effectors that act against the nematode and effectors that disrupt the nematode feeding site.

The heterologous DNAs may encode a product that is toxic to the plant cells, as described in U.S. Pat. No. 5,750,386 to Conkling et al. A wide variety of protein or peptide products which are toxic to plant cells can be used, including (but not limited to) enzymes capable of degrading nucleic acids (DNA, RNA) such as nucleases, restriction endonucleases, micrococcal nuclease, Rnase A, and Barnase (*Bacillus amyloliquefaciens* RNAse); enzymes which attack proteins such as trypsin, pronase A, carboxypeptidase, endoproteinase Asp-N, endoproteinase Glu-C, and endoproteinase Lys-C; ribonucleases such as RNase CL-3 and RNase $T_1$, toxins from plant pathogenic bacteria such as phaseolotoxin, tabtoxin, and syringotoxin; lipases such as produced from porcine pancrease and *Candida cyclindracea*, membrane channel proteins such as glp F and connexins (gap junction proteins), and antibodies which bind proteins in the cell so that the cell is thereby killed or debilitated. Genes which produce antibodies to plant cell proteins can be produced as described in Huse, W. et al. (1989) Science 246:1275–1281. Proteins to which such antibodies can be directed include, but are not limited to, RNA polymerase, respiratory enzymes, cytochrome oxidase, Krebs cycle enzymes, protein kinases, aminocyclopropane-1-carboxylic acid synthase, and enzymes involved in the shikimic acid pathway such as enolpyruvyl shikimic acid-5-phosphate synthase. In preferred embodiments, the heterologous DNA is an anti-apoptosis gene (Dickman, M. B. et al. (2001) Proc. Natl. Acad. Sci. 98:6957), a gene involved in the hypersensitive response, a gene involved in MAPK signal transduction, or a gene encoding an RNA interference construct that down-regulates a gene needed for feeding site establishment (Campbell, M. A. et al. (2002) Transgenic Res. 11 (6):599).

Note that the toxic product may either kill the plant cell in which it is expressed or simply disable the cell so that it is less capable of supporting the pathogen. It is preferred that the plant-toxic product be non-toxic to animals, and particularly be non-toxic to humans.

The heterologous DNA may encode any other product disruptive of nematode attack, including but not limited to those described in U.S. Pat. No. 5,589,622 to Gurr et al. (e.g., products toxic to the nematode). Thus the heterologous DNA may encode a *Bacillus thuringiensis* crystal protein toxic to insects. Strains of *B. thuringiensis* which produce polypeptide toxins active against nematodes are disclosed in U.S. Pat. Nos. 4,948,734 and 5,093,120 (Edwards et al.). Additionally, the heterologous DNA may encode other natural pesticides such as that found in *cyanobacterium Nostoc* strain ATCC 53789 (Biondi et al. (2004) Appl. Environ. Microbiol. 70(6):3313).

Again note that the toxic product may either kill the nematode attempting to feed on the plant cell in which it is expressed or simply disable the nematode so that it is less capable of feeding on the plant cell or establishing a feeding site. For example, the heterologous DNA may encode a peptide, antibody or the like that disrupts feeding by interacting with the ingestion or digestion of food such as one of the antibodies described for soybean cyst nematode including that against the dorsal pharyngeal gland (Atkinson et al., 1988 Annals of Applied Biology 112:459–469), using the procedures for transgenic expression of antibodies in plants described by Hiatt, A. et al. (1989) Nature 342:76–78).

Again it is preferred that the nematode-toxic product be non-toxic to other animals, and particularly be non-toxic to birds, reptiles, amphibians, mammals and humans.

Plant transformation is achieved via known methods of using expression vectors. Expression vectors generally include at least one genetic marker, operatively linked to a regulatory element (a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a coding sequence in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase, chloramphenicol and acetyltransferase (Jefferson, R. A. (1987) Plant Mol. Biol. Rep. 5:387; Teeri et al. (1989) EMBO J. 8:343; Koncz et al. (1987) Proc. Natl. Acad. Sci. USA 84:131; and DeBlock et al. (1984) EMBO J. 3:1681).

Also available are in vivo methods for visualizing GUS activity that do not require destruction of plant tissue (Molecular Probes publication 2908, Imagene Green™ p. 1–4 (1993); and Naleway et al. (1991) J. Cell Biol. 115:151a).

Additionally, a gene encoding Green Fluorescent Protein (GFP) has been utilized as a marker for gene expression in prokaryotic and eukaryotic cells (Chalfie et al. (1994) Science 263:802). GFP and mutants of GFP may be used as screenable markers.

Numerous methods for plant transformation have been developed, including biological and physical plant transformation protocols. See, for example, Miki et al., "Procedures for Introducing Foreign DNA into Plants" in Methods in Plant Molecular Biology and Biotechnology, Glick, B. R. and Thompson, J. E. Eds. (CRC Press, Inc. Boca Raton, 1993) pages 67–88.

One method for introducing an expression vector into plants is based on the natural transformation system of *Agrobacterium*. See, for example, Horsch et al. (1985) Science 227:122. *A. tumefaciens* and *A. rhizogenes* are plant pathogenic soil bacteria which genetically transform plant cells. The Ti and Ri plasmids of *A. tumefaciens* and *A.*

*rhizogenes*, respectively, carry genes responsible for genetic transformation of the plant. See, for example, Kado, C. I. (1991) Crit. Rev. Plant Sci. 10:1. Descriptions of *Agrobacterium* vector systems and methods for *Agrobacterium*-mediated gene transfer are provided by Gruber Miki et al., supra. and Moloney et al. (1989) Plant Cell Reports 8:238. See also, U.S. Pat. No. 5,563,055, issued Oct. 8, 1996.

Several methods of plant transformation collectively referred to as direct gene transfer, have been developed as an alternative to *Agrobacterium*-mediated transformation. A generally applicable method of plant transformation is microprojectile-mediated transformation wherein DNA is carried on the surface of microprojectiles measuring 1 to 4 μm. The expression vector is introduced into plant tissues with a ballistic device that accelerates the microprojectiles to speeds of 300 to 600 m/s which is sufficient to penetrate plant cell walls and membranes (Sanford, J. C. (1990) Physiol. Plant 7:206; Klein et al. (1992) Biotechnology 10:268; U.S. Pat. No. 5,015,580, issued May 14, 1991; and U.S. Pat. No. 5,322,783, issued Jun. 21, 1994).

Another method for physical delivery of DNA to plants is sonication of target cells (Zhang et al. (1991) Bio/Technology 9:996). Alternatively, liposome or spheroplast fusions have been used to introduce expression vectors into plants (Deshayes et al. (1985) EMBO J. 4:2731; Christou et al. (1987) Proc. Natl. Acad. Sci. USA 84:3962). Direct uptake of DNA into protoplasts using $CaCl_2$ precipitation, polyvinyl alcohol or poly-L-ornithine has also been reported (Hain et al. (1985) Mol. Gen. Genet. 199:161; and Draper et al. (1982) Plant Cell Physiol. 23:451). Electroporation of protoplasts and whole cells and tissues have also been described (Donn et al., in Abstracts of VIIth International Congress on Plant Cell and Tissue Culture IAPTC, A2-38, p 53 (1990); D'Halluin et al. (1992) Plant Cell 4:1495–1505; and Spencer et al. (1994) Plant Mol. Biol. 24:51–61).

A transformed soybean cell is one which has been transformed or transfected with DNA constructs as described herein. The transformed or transfected cell is then clonally propagated using known methods to generate a soybean plant. Tissue culture of various tissues of soybeans and regeneration of plants therefrom is well known and widely published. For example, reference may be had to Komatsuda, T. et al., Crop Sci. 31:333–337 (1991); Stephens, P. A., et al., Theor. Appl. Genet. (1991) 82:633–635; Komatsuda, T. et al., Plant Cell, Tissue and Organ Culture, 28:103–113 (1992); Dhir, S. et al., Plant Cell Reports (1992) 11:285–289; Pandey, P. et al., Japan J. Breed. 42:1–5 (1992); and Shetty, K., et al., Plant Science 81:245–251 (1992); as well as U.S. Pat. No. 5,024,944 issued Jun. 18, 1991 to Collins et al., and U.S. Pat. No. 5,008,200 issued Apr. 16, 1991 to Ranch et al.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

The Examples set forth herein describe in detail the isolation and characterization of duplicate copies of the FGAM synthase gene from soybean. This gene was identified by differential display analysis and confirmed by RT-PCR to be upregulated within the feeding sites of *Heterodera glycines* in soybean roots (Vaghchhipawala et al. (2001), supra). Isolation and characterization of the gene from the Williams 82 cultivar of soybean revealed the presence of three copies of the gene, two with high sequence homology and one distantly related. The presence of multiple gene copies was anticipated given the duplicated nature of the soybean genome (Shoemaker, R. C. et al. (1996) Genetics 144:329–338).

As is discussed in the Examples, the FGAM1 gene was encompassed within BAC 53M17, while FGAM2 resides within the BAC 42013/52C8 contig. The high sequence similarity between the genes suggests that the two loci have likely arisen by gene duplication. The degree of sequence identity between the two open reading frames (95.5%) and promoter regions (85%) implies that the duplication occurred fairly recently in evolutionary terms. Although the two gene copies show high protein sequence identity, an estimation of the coalescence time following the procedure of Lynch et al. (Science 290:1151–1155 (2000)) yields a date of approximately 11 Mya. The two loci apparently continue to carry out duplicate functions in differing spatial and temporal patterns or in response to varying stimuli.

Evidence for multi-gene copies in soybean is extensive. A recent study (Jin et al., 1999) reported at least 12 classes of β-1,3-glucanase genes displaying divergent gene expression patterns. Members of a BURP domain-containing protein family, from soybean were also shown to possess diverse expression patterns (Granger, C. et al. (2002) Genome 45:693–701). Mahalingam, R. et al. (1999) MPMI 12:490–498, identified two copies of a polygalacturonase gene, also from soybean, with expression up-regulated during syncytium establishment. Yamamoto, E. (2001) Mol. Biol. Evol. 18:1522–1531, identified three soybean orthologs of *A. thaliana* receptor-like protein kinases showing high sequence homology and predicted to have arisen from recent duplication events. The advantage of gene redundancy in soybean and other plant genomes is not known, but it has been suggested that members of a gene family generally retain a set of standard functions but acquire unique expression patterns and responses to environmental stimuli. It has been proposed that tissue specificity is an early step in functional divergence of a gene family, while divergence at the amino acid level occurs later (Pickett, F. B et al. (1995) Plant Cell 7:1347–1356). The differential expression of FGAM1 and FGAM2 and the observed divergence between their promoters are consistent with this hypothesis.

The essential function provided by FGAM synthase would predict its activity in areas of rapid cell proliferation. These tissues should include reproductive organs and apical and lateral meristems. This anticipated pattern of expression was evident in the GUS expression assays for FGAM1 full-length promoter (Pr1-2.5). A surprising exception was the pollen sacs, in which no FGAM1 expression was detected. Possibly, sequences for anther expression were present further upstream to the region tested and were omitted from the tested constructions, or a different FGAM synthase copy might be expressing within anther tissues. Lack of detectable GUS expression in the FGAM1 promoter deletions (Pr1-1.5 and Pr1-1.0) suggests that enhanced expression levels or tissue specificity of expression may reside within the interval 1.5 kbp upstream to the translation start site.

To investigate the divergent expression that has arisen between the two loci, we focused on promoter sequence differences. Alignment of promoter sequences revealed a FGAM1 stress response element close to the translation start site. Moreover, FGAM2 promoter constructions showed no GUS expression, suggesting that expression of this locus is much lower or responsive to particular stimuli.

Sequences responsible for feeding site GFP expression were located within an upstream 1.0-kbp interval present in both promoters. Observation of enhanced GFP expression in feeding sites from all constructions, and the considerable sequence homology within the upstream 1.0-kbp interval that confers nematode-responsive expression, suggest that nematode-inducible activity was acquired prior to the gene duplication event.

It is conceivable that nematode responsiveness in the expression of FGAM synthase has facilitated co-evolution of the host-nematode interaction. Purine biosynthesis gene expression in the root has already been shown to be inducible by *Rhizobium* (Schnorr, K. M. et al. (1996) Plant Molec. Biol. 32:751–757). In fact, several examples of reprogrammed plant gene expression have been found in response to nematode infection (Gheysen, G. et al. (2002) Ann. Rev. Phytopathol. 40:191–219). Juergensen, K. et al. (2003) Plant Physiol 131:61–69, demonstrated activated expression of AtSuc2, which mediates the transmembrane transfer of sucrose into syncytia that acts as nutrient sinks for the nematode. Down regulation of a novel Glycine max ethylene-responsive element-binding protein 1 (GmEREBP1) has also been reported. This protein binds to GCC motifs located within PR gene promoters in *H. glycines*-infected soybean roots during a susceptible interaction (Mazarei, M. et al. (2002) MPMI 15:577–586) to undermine host defenses. Vercauteren, I. et al. (2002) MPMI 15:404–407, report the up-regulation of a pectin acetylesterase gene in feeding sites of root and cyst-knot nematodes. This gene encodes a pectin-degrading enzyme that may be involved in softening and loosening the primary cell wall in nematode-infected plant roots, leading to expansion of the syncytium. These reports reflect the very broad spectrum of genes thought to be redirected in expression by the nematode for feeding site establishment. The feasibility of disrupting gene expression patterns essential to feeding site establishment as a method of plant protection has not been fully assessed.

Sijmons, P. C. et al. (1991) Plant J. 1: 245–254, were first to document in detail the requirements for successful infection of *Arabidopsis* by economically important nematodes. In Golinowski, W. et al. (1996) Protoplasma 194:103–116; and Golinowski, W. et al. (1997) in Cellular and molecular aspects of plant-nematode interactions (C. Fenoll et al. (eds.), pp. 80–97, ultrastructural studies were undertaken on root cellular architecture to follow the course of development of *H. schachtii* in *Arabidopsis* roots. The nematode developmental life-cycle (~6 weeks) of *H. schachtii* is similar to that of *Heterodera glycines*. Likewise, the sequence of changes in *Arabidopsis* root cell morphology appears to follow a similar course to that in soybean roots. For these reasons, it appears that the observations made in *Arabidopsis* are likely to parallel events in the infected soybean root.

Interestingly, the expression profiles observed in the full length and deletion constructions for the FGAM1 promoter were similar to the pattern reported for the promoter of gene pyk20, isolated from *Arabidopsis thaliana* by a promoter tagging strategy (Puzio, P. S. et al. (2000) Plant Sci. 157: 245–255). This approach was used to identify genes that were active in nematode feeding sites. The investigators detected expression within the feeding sites as well as floral organs, and a wound response within leaves. Likewise, they reported a region of 963 bp upstream to the first ATG of pyk20 that was sufficient to direct expression within the nematode feeding site in *Arabidopsis* roots. The lack of expression within feeding sites by vector control constructions (35S::GFP) in our study agrees with previous published data (Urwin et al., 1997, Plant J. 12(2):455–61 and van Poucke et al., 2001, Meded Rijksuniv Gent Fak Landbouwkd Toegep Biol Wet. 66(2b):591–8).

Opperman, C. H. et al. (1994) Science 263:221–223, reported a requirement of 300 bp of upstream sequence to the TobRB7 gene of tobacco for localized expression in *Meloidogyne*-induced giant cells. Moreover, Escobar, C. et al. (1999) MPMI 12:440–449, identified a sequence 111 bp upstream of the TATA box where nuclear proteins from nematode-induced galls formed DNA protein complexes. These reports indicate that putative nematode responsive domains are generally present in regions of the promoter very close to the transcription initiation sites. It is conceivable that an array of common nematode responsive promoter domains serve as the primary means of coordinating plant gene expression during syncytium establishment.

Based on observations described herein, it appears that the FGAM1 locus likely serves housekeeping functions, while FGAM2 may respond to specific environmental stimuli. Yamamoto, E. et al. (2000) MPMI 12: 440–449, reported the cloning of two identical CLAVATA 1-like genes from soybean which show differential expression patterns and suggest that the function of the two genes is slightly different in different organs. In contrast, both FGAM full-length promoters (and deletion fragments thereof) were found to be nematode inducible, indicating that the nematode inducible domain is located in the 1.0 kbp domain immediately 5' to the translation start site.

The present invention is explained in greater detail in the following non-limiting Examples.

EXAMPLES

Example 1—Materials and Methods

Vectors and Strains

The genomic copies of FGAM synthase were isolated from a bacterial artificial chromosome (BAC) library prepared from the partial Hind Ill digestion of genomic DNA of the soybean line 'Williams 82'(Marek, L. F. (1997) Genome 40:420–427). Gene promoter constructions utilized the vector pCAMBIA 1303. Transgene constructions were introduced into ELECTROMAX DH10B cells (Life Technologies, USA) of *Escherichia coil* via electroporation.

DNA Gel Blot Analysis, PCR and DNA Sequencing Procedures

DNA gel blot analysis was carried out using standard procedures (Sambrook, J. et al. (1989) Molecular Cloning: A Laboratory Manual, 2nd ed., Cold Spring Harbor Laboratory, Cold Spring Harbor, N.Y.). DNA sequencing was accomplished using the fluorescently-labeled primer cycle sequencing kit with 7-deaza-dGTP (Amersham Intl., Buckinghamshire, England) in an ALFexpress automated sequencer (Pharmacia, Biotech AB, Umeå, Sweden). The polymerase chain reaction (PCR) was carried out using genomic DNA from transgenic *Arabidopsis* leaves prepared according to published protocol (Li, J. et al. (1998) in Molecular Cloning: A Laboratory Manual, 2nd ed., Cold Spring Harbor Laboratory, Cold Spring Harbor, N.Y.) as template. Primers were designed from the uidA sequence to amplify a product of approximately 1189 bp.

Genomic, Plasmid and BAC DNA Preparations and Sequence Homology Searches

Genomic DNA was prepared by the method of Vallejos, C. E. et al. (1992) Genetics 131:733–740. Plasmid DNA preparations were carried out using the CONCERT™ plasmid miniprep kit (Life Technologies, USA), while BAC DNA was prepared using a modified alkaline lysis protocol (Felicielo, I. et al. (1993) Anal. Biochem. 212:394–401). GCG package software "SEQWEB" function "Bestfit" was used to identify sequence homologies, and the "motifs" function was used to locate protein motifs of interest.

Preparation of Promoter Constructions

The subcloning of the promoter region was carried out in the vector pCAMBIA1303, which incorporates the reporter genes β-glucuronidase (GUS) and enhanced green fluorescent protein (GFP) under the control of the CaMV 35S promoter. Cloning was accomplished by excising the 35S promoter from the vector by digestion with enzymes BamHI and NcoI, and introducing putative promoter fragments from the two identified FGAM synthase genes, FGAM1 and FGAM2. Promoter inserts (2.48 kbp) and their derived truncations were generated by PCR amplification with primers designed to contain BamHI and NcoI restriction sites.

Generation of *Arabidopsis* Transformants

The transformation of *Arabidopsis thaliana*, grown in a 16-hr day, 8-hr night light regime, was carried out using the floral dip method (Clough, S. J. (1998) Plant J. 16:735–743). The *Agrobacterium tumefaciens* strain C58C1 (provided by Dr. Thomas Clemente, University of Nebraska-Lincoln) was used to transform *Arabidopsis* ecotype Columbia. Transgene constructions were mobilized into the *Agrobacterium* strain via electroporation. Upon transformation, selection of transgenic plants was carried out by plating surface-sterilized seeds on 0.5×MS-B medium with 2% (w/v) sucrose, vitamins and 20 mg/L Hygromycin. Selected plants were subjected to GUS staining (Jefferson, R. A. et al. (1987) EMBO J. 6:3901–3907), PCR analysis, and DNA gel blot analysis before inclusion in the nematode assay.

GUS Staining and Microscopy Procedures

Plant tissues were immersed in X-Gluc (0.8 mg/ml) solution and kept overnight at 37° C. for color development. After staining, 70% (v/v) ethanol was added for clearing of pigments, following the procedure of Jefferson et al. (1987), supra. The infection of transgenic *Arabidopsis* roots by *Heterodera schachtii* was examined for GFP fluorescence with a Confocal Laser Scanning Microscope (CLSM) (Bio-Rad, USA).

*Heterodera schachtii* Infection Assays of *Arabidopsis* Transformants

Seeds from confirmed transgenic *Arabidopsis* plants were germinated on selective media as described above, then transferred to individual wells of a 12-well petri plate containing 1.5 ml of a modified Knop's medium (Sijmons et al. (1991), supra) minus antibiotics. Infection was carried out on 11 to 13-day-old seedlings whose roots had penetrated into the medium. Each 12-well plate contained 10 individual $T_1$ transgenic seedlings derived from one independent transformant; the last two plants in the plate served as uninoculated controls. This system, following the procedure of Baum, T. J. et al. (2000) J. Nematol. 32:166–173, provided ample experimental replications without undue contamination. The plants were inoculated near the roots with 50–100 surface-sterilized J2 juveniles of *Heterodera schachtii* suspended in 1.5% (w/v) low melting agarose. After 6–8 days incubation in a growth chamber at 25° C. and 16 hr daylength, allowing for feeding site establishment on the roots, plants were examined for GFP expression at root feeding sites by confocal laser scanning microscopy. Subsequently, GUS expression was assayed by filling the entire well with X-Gluc staining solution and incubating at 37° C. overnight. Clearing of tissues involved adding 70% (v/v) ethanol, and cleared roots were observed under the dissecting microscope.

Surface Sterilization of *Heterodera schachtii* J2 Juveniles

Worms freshly hatched after a 2–3-day incubation in a hatch chamber in 3.14 mM $ZnSO_4$ were used for inoculation. Juveniles were counted in a haemocytometer and approximately 100,000 individuals were placed in a sterile 50-ml centrifuge tube. The samples were washed once in sterile distilled water by pelleting at 1500–2000 rpm for 3 minutes in a centrifuge using a swinging bucket rotor and no brake. The nematodes were resuspended in 50 ml of 0.001% Hibitane (Chlorhexidine, diacetate salt, Sigma #C6143) for 30 min mixing continuously. The sample was centrifuged at 1500 rpm for 3 minutes and resuspended in 50 ml of 0.01% (w/v) $HgCl_2$. This suspension was incubated for 7 minutes, including the time to pellet the worms and remove supernatant. The sample was centrifuged to remove the $HgCl_2$, followed by 3 washes with sterile distilled water. After the last wash, enough 1.5% (w/v) LMP agarose was added to achieve the desired final concentration of nematodes, and the sample was maintained at 37° C. The slurry was pipeted over roots in each well. J2 motility was observed after the LMP agarose had solidified.

Example 2—Assembly of Soybean FGAM Synthase Gene Contigs

The sequence of FGAM synthase cDNA (AF000377) was used to generate two primers for use in RT-PGR. Primer 113: 5'-GGT AU GAT GGA GGG AAA GAC AG-3' (SEQ ID NO: 19) and Primer 114: 5'- GCC ATC TCT AAG GCA GAA ACT AG-3' (SEQ ID NO: 20) were used to screen soybean genomic BAG library DNA pools by PCR. The search yielded four putative hits and the corresponding BAG clones 81J4, 42O13, 53M17, and 52C8 were selected. The four BAG clones were digested with NotI enzyme and subjected to pulsed field gel electrophoresis to estimate insert sizes ranging from 110 kb to 160 kb. To assemble the BAG clones into contigs, multi-enzyme DNA digestions were separated by agarose gel electrophoresis. The BAG clones 42O13 and 52C8 were found to share several bands in common, while the fingerprint of BAG 53M17 shared fewer bands. BAG 81J4 had a distinct banding pattern. Overlaps were confirmed by DNA gel blot hybridization. When probed with the FGAM synthase cDNA clone (890 bp), BACs 42O13 and 52C8 produced identical hybridization patterns, while the pattern produced by BAG 53M17 differed. A very faint hybridization signal was detected in BAG 81J4, suggesting that the FGAM homology contained within this locus was weak. The two distinct forms of FGAM synthase represented in BACs 53M17 and 42O13/52C8 were henceforth referred to as FGAM1 and FGAM2, respectively. Digestion of Williams 82 genomic DNA with HhaI also revealed 2 prominent and one faint band, consistent with presence in the genome of two homologous loci and one divergent sequence.

Genetic mapping of the original FGAM cDNA in the soybean genome indicated that at least one copy of the FGAM loci is derived from Linkage Group G at the same map location as the major SCN resistance gene, Rhg1. Mapping data were derived from a mapping population of 57 $F_2$ individuals and a RIL mapping population of 100 individuals (Vaghchhipawala et al. (2001) supra). BAC analyses confirmed that the FGAM locus is duplicated. However, the location of the duplicate FGAM locus was not determined. Overlapping fragment analysis was used to determine full-length genomic sequence of genes FGAM1 and FGAM2 using the FGAM synthase cDNA clone to generate end probes. At the 5' end of each gene, approximately 2.5 kb of promoter sequence was also determined.

Example 3—Characterization of the Duplicate FGAM Synthase Loci

DNA sequence analysis of FGAM1 (Genbank AY178840) and FGAM2 (Genbank AY178839) revealed an open reading frame of 3132 bp and 3940 bp respectively (see FIGS. 1A and 1B). The two DNA sequences were 95.5% identical. Cluster analysis to assess amino acid sequence conservation among homologous FGAM synthase sequences available for soybean, Drosophila, Human and E. coli revealed highest sequence conservation among these genes within the ATP-binding domain and three glutamine binding domains as shown in FIG. 2A. Dendrogram analysis of 12 FGAM sequences from Genbank revealed a separate clustering of microbial and higher eukaryotic sequences. Among the higher eukaryotic genes identified, plant and animal sequences form distinct groups. Sequence analysis of the 2.5-kbp promoter region of the FGAM1 and FGAM2 genes revealed 85% identity. Scanning of the promoter sequences for various motifs revealed the presence of a stress response element (STRE) (Schuller, C. et al. (1994) EMBO J. 13:4382–4389) within the promoter of gene FGAM1 (nt 2361–2369 from 5' end) with 97% conservation of the consensus. This element is shown to activate transcription of a yeast gene in response to a variety of stress stimuli (Schuller et al. (1994), supra). Alignment of the two promoter sequences to the wun1 wound-inducible promoter from potato, inducible during cyst nematode infection (Hansen, E. et al. (1996) Physiol. Mol. Plant Pathol. 48:161–170), revealed a 39-bp interval with 95% sequence identity within the FGAM1 promoter but only 68% identity within the FGAM2 promoter (FIG. 2B).

Example 4—Promoter Analysis in the *Arabidopsis thaliana-Heterodera schachtii* System To determine which FGAM synthase gene was responsive to nematode infection, we conducted transgenic promoter analysis in the established *A. thaliana-H. schachtii* system (Sijmons et al. (1991), supra). This system has been reported to parallel cellular events of the soybean-SCN infection process (Golinowski, W. et al. (1996) Protoplasma 194: 103–116). To determine which promoter intervals were serving to modify gene expression within syncytia, we developed two deletion constructs from each full-length promoter. The deletions were made at the 5' end of each original 2.48-kbp promoter, leaving 1.5-kbp and 1.0-kbp sequences immediately 5' to the translation start site in association with GUS (uidA) and gfp reporter genes as diagrammed in FIG. 3. The most divergent interval between the two promoters was located between nucleotides −1483 and −1983 (in relation to the +1 translation start site) in the FGAM2 promoter and nucleotides −1314 and −1014 (in relation to +1 start site) in the FGAM1 sequence. Within this region exists a stretch of sequence of 70 nucleotides in the FGAM2 promoter that is absent from the FGAM1 promoter. To test whether the divergent sequences might account for nematode responsiveness, two deletion constructions containing this region, Pr1-1.5 (FGAM1) and Pr2-1.5 (FGAM2), were derived. The effect of deleting these divergent regions was assessed with constructions Pr1-1.0 and Pr2-1.0 (FIG. 3).

Example 5—FGAM1 and FGAM2 Promoter Expression

Transformants for the six promoter constructions of FGAM1 and FGAM2, as well as the vector control, were stained with X-Gluc solution. Two independent vector-transformed control lines, harboring the 35S promoter fused to GUS-GFP, produced GUS staining in leaves, inflorescence, stem and roots. Five independent transformants containing the full length (2.48-kbp) FGAM synthase promoter from gene FGAM2 (Pr2-2.5) were evaluated for GUS expression, and none produced detectable GUS staining in any part of the seedling including inflorescence. The same results were obtained for the four independent transformants of deletion construction Pr2-1.5 and for seven transformants of construction Pr2-1.0.

Experiments with the 2.48-kbp full-length FGAM1 promoter (Pr1-2.5) produced four independent transformants. With some minor plant variation, Pr1-2.5 transformants showed GUS staining in leaf margins and veins, the root tip and lateral root meristems and inflorescence with the exception of anthers. The FGAM1 deletion constructions, Pr1-1.5 (two events) and Pr1-1.0 (two events) showed no visible GUS staining anywhere in the seedling including flowers. Non-transformed seedlings produced no GUS staining. These results imply that the two promoters differ markedly in strength as a consequence of sequences located more than 1.5 kbp from the translation start site in FGAM1. They also indicate that sequences located more than 1.5 kbp from the translation start site are important in housekeeping growth functions unrelated to nematode responsive expression in established feeding sites.

Example 6—Promoter Expression Analysis in *H. schachtii*-inoculated *Arabidopsis* roots Twelve individual $T_3$ progeny per gene construction were used in the *H. schachtii* infection assay carried out in twelve-well plates. Two plants served as uninoculated controls. Each plant was infected with 50–100 J2 juveniles, maintained in the growth chamber for 6 days, and then observed under a confocal laser-scanning microscope for GFP expression within feeding sites.

Roots of the vector control showed a uniform green fluorescence, and did not show significant elevation of GFP fluorescence at the sites of infection. Localized at the region of the root where a nematode had established a syncytium, a significant elevation of GFP expression above background was observed in all FGAM1 and FGAM2 promoter constructions. This observation was documented at least five times in each inoculated well (50 replicates for each independent transformant) for all promoter constructions. No localized elevation of GFP expression was seen in the uninoculated controls. Instances in which the nematode had penetrated the root tissue but had not yet established a feeding site showed no localized elevation of GFP. This observation suggests that the establishment of a feeding site was necessary for the enhancement of local GFP expression levels, and indicates that the elevated expression was not simply a localized wound response.

Example 7—Wound Response

Sequence homology data indicated that the FGAM1 gene promoter contains a 39-bp sequence with 95% sequence identity to the wun1 wound inducible promoter from potato. The FGAM2 gene promoter displayed only 68% sequence identity to the wun1 promoter. A leaf from each transformant was excised from the seedling and assayed for GUS expression. Of all transformants tested, one containing the full-length FGAM1 promoter construction (Pr1-2.5) showed what appeared to be a wound response. The excised leaf produced a visible staining pattern in the area around the wounded edge, while the remainder of the leaf remained unstained. This observation suggests that the FGAM1 promoter effects a weak wound response. None of the transformants containing the FGAM2 full length or deletion promoter constructions showed evidence of wound response. These results, again, imply that the nematode responsive expression observed in all transformants did not represent a general wound response.

The invention claimed is:

1. An isolated nucleic acid molecule comprising a soybean promoter sequence that comprises a nematode responsive domain, wherein the promoter sequence comprises a sequence selected from the group consisting of: Pr1-1.0 (the sequence from nucleotides 1790 to 2483 of SEQ ID NO: 2), Pr2-1.0 (the sequence from nucleotides 1551 to 2547 of SEQ ID NO: 1), Pr1-1.5 (the sequence from nucleotides 1271 to 2483 of SEQ ID NO: 2), Pr2-1.5 (the sequence from nucleotides 991 to 2547 of SEQ ID NO: 1), Pr1-2.5 (the sequence from nucleotides 124 to 2483 of SEQ ID NO: 2) and Pr2-2.5 (the sequence from nucleotides 19 to 2547 of SEQ ID NO: 1).

2. The nucleic acid molecule of claim 1, further comprising a heterologous DNA operatively linked to the promoter.

3. The nucleic acid molecule of claim 2, wherein the heterologous DNA encodes a product that is disruptive of nematode attack.

4. The nucleic acid molecule of claim 3, wherein the heterologous DNA encodes a product that is toxic to a plant cell.

5. The nucleic acid molecule of claim 4, wherein the heterologous DNA comprises a gene selected from the group consisting of anti-apoptosis genes, genes involved in the hypersensitive response, genes involved in MAPK signal transduction, and genes for RNA interference that downregulate a gene needed for nematode feeding site establishment.

6. The nucleic acid molecule of claim 3, wherein the heterologous DNA encodes a product possessing anti-helminthic properties.

7. The nucleic acid molecule of claim 6, wherein the heterologous DNA encodes a Bacillus thuringiensis crystal protein toxic to nematodes.

8. A transfected soybean cell comprising the nucleic acid molecule of claim 1.

9. A transgenic soybean plant comprising the plant cell of claim 8.

10. A method of reducing nematode infection of a soybean plant comprising transfecting cells of the soybean plant with the nucleic acid molecule of claim 3.

* * * * *

SEQUENCE LISTING

```
<160> NUMBER OF SEQ ID NOS: 18

<210> SEQ ID NO 1
<211> LENGTH: 5684
<212> TYPE: DNA
<213> ORGANISM: Glycine max
<220> FEATURE:
<221> NAME/KEY: CDS
<222> LOCATION: (2548)..(5682)

<400> SEQUENCE: 1
ttgtttttta ttttttaaaa aagttttgac atgtacctgt aatataatat ccatgtagga      60 ggcttttta acaactgtat cccatataac atatcatgtg agaatctata gtccacttta     120
taagaatgtg tgaggtcagg tggattaaca tttaacaatt ttcctatttt cccatgcata     180
aaaaaaaaac atttatcaat ttttccacgt agtccatttt ttttaaaaaa agtaatgcga     240
catgtgaaat tgccatataa tgattttgat aggatgtctt aaaacagtct cattttaata     300 aaatattta aaataatatc atttaattat tatttctaat tttgcctcaa ttttatcaat      360
cagttaaaga agtcacgaga ttttcatata tctattttat ttcaatattt aaattgaaac     420
tttcaattga ttttttttatt gtcattcatt ctgtaaccaa taaaattctt tgaattttt      480 gagattgatt tctcgtatgt taaattataa tatgacaaca ttatatttaa tttttcttaa     540
ttacaaagtt ttcaataaca aaattggatc garagaraat gtcatcatat agtaacttt       600 tttaaagatg acacataata acttgcactt taaaaaaaga cttgcacttt gcagatcaag     660
grcataaatt aattttagc atatgtctga atacgcgtta tcaaaaaata aatcaaacgt      720
ctaatgcaaa agtcactctc acaactcaca agtttctgtg tcttttggga agttgatgtt    780
aaaatgagag aatgaaccga tatatatata tatatatata tatatatcaa ttgcgatgtt    840
aagattatta ttgaagtaga cacatgacaa gatagaaaaa atttacttat aaaagaaat     900 aataacatgc aaatgaatta tctcagtcaa gtaaaaattt taatttatta ttttttgaa      960 aggcaaaaat ttaaatttat tatataagaa tgaatcttat actttatata actatagaag    1020
ataaagttat attgagatat tttaactcat tagttatcaa tttaacgatt tcaacttttt   1080
ataaaccaca ggcaatttga tagaaacgtt aaaactttaa aaagaaaatc caaactgtac    1140
ttacagttcc cacagggcca attctaccta gagttttagt gaagagccaa ttctaatttt     1200
ttttcctcct ataaaatcaa atacacacat ttttaataaa agttttttt taaatctaga     1260 ttacaaaaga gattctgaat taaaaatatt aaaagtcact tttcactgcg tttaaaagtc    1320
atacaattgg ctgtaaaaaa aaacagtcat acaattatta cattgcacca aatatacatc    1380
ttattattat ctgatatgaa ttaaatatta tacatgatta aagtctattt tgctcttatc    1440
```

```
                                                                 -continued
ttatttatca tatattatta tttgatttat tatctttctt taaaaaaatc tcattcttat   1500 tttatttttat catgttctta ttttgttgtc gactcctctc ttattttaac aagttttca    1560 tagataataa ttttttttcat aaataaaagt taacgatact tgaaaatact tctcaaacta   1620
acactagttt ttactttttt ttttatttaa aaatatctta gtaatttaca gcttcgagtt   1680
tcacaaagaa acaagtgtgt ttatatatag gcttctttta tgaactttgg attacgcatc   1740
cgattcggct aaaaaaggta agcatcggca gacaaagaaa tcgtcgataa aacagagaaa   1800
atataaaaat agcgccaacg caaccaatag ttaaattgaa agggtgaaaa cttttaatat   1860
ttttactcgt ttgatttgaa gggagagaaa gagagtacta agtggctagt agggttttat   1920
tgtgtgccac accaaaaccc tctcttcgtt ttacgtcact tccacactca ctctgttttg   1980
ttctgctact cttcgattct acttcttcta cttgattccc acatttctta ttttgcgtag   2040
tgaatatttt tttcttcttc ttttttttaga gctttcccac acttgatcga ggatatggcg   2100
actgcgacgg aatttggggt atcgcaattc ttgaaggttt gattttaatt cctctcttgg   2160
aattaacctc atatgctgca ccccttttgt taatttatta attgttgttc ttgttggggg   2220
aaaaaggtca tgctttgatg ctgcagtgac atgtttcgat gcatctttgc ttattgggtt   2280
ttgtgatttt ggtttcaggg gacctccagg caaactctgt ttttgtagaa gaagcctcag    2340
aggcagaaaa gtcgcatgct ttggggtgca ctctggaatc ggaattgggg tctgggatca    2400
actcgcagag ctttgccttt aaggtgtcag actcaggaaa atcccagagc tgtggtttct   2460
ggtggcgtaa gcagttctgt agaggagcaa cctgccttgt ttgagaagcc cgcttccgaa   2520
gttgttcatt tgtaccgtgt cccgttt atg caa gaa agt gca gct gct gag ctt   2574
                              Met Gln Glu Ser Ala Ala Ala Glu Leu
                               1               5 ttg aag gag gct caa gtg aaa atc tcc agt cag atc gtg gaa ata cta     2622
Leu Lys Glu Ala Gln Val Lys Ile Ser Ser Gln Ile Val Glu Ile Leu
 10              15                  20                  25 acg gag cag tgc tat aat gtt ggc ctt agt tcg caa ctt tcc ggt gga     2670
Thr Glu Gln Cys Tyr Asn Val Gly Leu Ser Ser Gln Leu Ser Gly Gly
                 30                  35                  40 aaa ttt tca gtt ctt gga tgg ctt ctt caa gaa aca ttc gag cct gag     2718
Lys Phe Ser Val Leu Gly Trp Leu Leu Gln Glu Thr Phe Glu Pro Glu
                     45                  50                  55 aat ctg gga act gag agc ttt ctt gag aag aag agg aag gag ggt ctg     2766
Asn Leu Gly Thr Glu Ser Phe Leu Glu Lys Lys Arg Lys Glu Gly Leu
             60                  65                  70 att cca gtt att gtt gaa gtt ggc ccc agg ttg tca ttc acc aca gca     2814
Ile Pro Val Ile Val Glu Val Gly Pro Arg Leu Ser Phe Thr Thr Ala
 75                  80                  85 tgg tct act aat gct gtt gca att tgc cag gcc tgt ggt ttg aca gaa     2862
Trp Ser Thr Asn Ala Val Ala Ile Cys Gln Ala Cys Gly Leu Thr Glu
 90                  95                 100                 105 gtt aac cgt ttg gaa cgg tcc agg agg tac ttg ttg ttc acc acc act     2910
Val Asn Arg Leu Glu Arg Ser Arg Arg Tyr Leu Leu Phe Thr Thr Thr
                110                 115                 120 gaa ctg caa gat tat caa atc aat gat ttt gca tct atg gtg cat gat     2958
Glu Leu Gln Asp Tyr Gln Ile Asn Asp Phe Ala Ser Met Val His Asp
                125                 130                 135 agg atg act gaa tgt gtt tat att cag aaa cta aca tcc ttt gag acc     3006
Arg Met Thr Glu Cys Val Tyr Ile Gln Lys Leu Thr Ser Phe Glu Thr
            140                 145                 150 agt gtt gtt ccg gag gag att cat tat ata cct gtc atg gag agg gga    3054
Ser Val Val Pro Glu Glu Ile His Tyr Ile Pro Val Met Glu Arg Gly
            155                 160                 165
```

-continued

| | |
|---|---|
| cga aag gca tta gaa gag att aat ttg gag atg ggt ttt gcc ttt gat<br>Arg Lys Ala Leu Glu Glu Ile Asn Leu Glu Met Gly Phe Ala Phe Asp<br>170                175               180              185 | 3102 |
| gac cag gat tta gaa tac tac acc aaa ctt ttc aga gaa gac att aag<br>Asp Gln Asp Leu Glu Tyr Tyr Thr Lys Leu Phe Arg Glu Asp Ile Lys<br>               190              195             200 | 3150 |
| cgc aac ccg aca aat gtg gaa ttg ttt gat ata gca cag tcc aac agt<br>Arg Asn Pro Thr Asn Val Glu Leu Phe Asp Ile Ala Gln Ser Asn Ser<br>205                210              215 | 3198 |
| gag cac agc aga cac tgg ttt ttt act gga aag att ttc att gat gga<br>Glu His Ser Arg His Trp Phe Phe Thr Gly Lys Ile Phe Ile Asp Gly<br>    220              225              230 | 3246 |
| cag ccc gtg aat aga act ctc atg cag att gtg aaa agt act ctg cag<br>Gln Pro Val Asn Arg Thr Leu Met Gln Ile Val Lys Ser Thr Leu Gln<br>235                240              245 | 3294 |
| gca aac cca aat aac tca gtt att ggc ttc aag gat aac tct agt gca<br>Ala Asn Pro Asn Asn Ser Val Ile Gly Phe Lys Asp Asn Ser Ser Ala<br>250                255              260             265 | 3342 |
| atc agg ggt tth cca gtg aag cag ctc cga cca gtt cag cct ggt tca<br>Ile Arg Gly Xaa Pro Val Lys Gln Leu Arg Pro Val Gln Pro Gly Ser<br>               270              275             280 | 3390 |
| gca tgt cca tta gaa gtt gca gtc cat gag tta gat atc ttg ttt aca<br>Ala Cys Pro Leu Glu Val Ala Val His Glu Leu Asp Ile Leu Phe Thr<br>           285               290             295 | 3438 |
| gct gaa aca cat aat ttt cca tgc gca gtg gca cct tat cct ggt gca<br>Ala Glu Thr His Asn Phe Pro Cys Ala Val Ala Pro Tyr Pro Gly Ala<br>        300              305              310 | 3486 |
| gag acg ggt gca gga ggt cgc att agg gat aca cac gct acc gga agg<br>Glu Thr Gly Ala Gly Gly Arg Ile Arg Asp Thr His Ala Thr Gly Arg<br>315                320              325 | 3534 |
| ggg tcc ttt gtc cag gca gct aca gct ggt tat tgc gtt ggg aat ctc<br>Gly Ser Phe Val Gln Ala Ala Thr Ala Gly Tyr Cys Val Gly Asn Leu<br>330                335              340             345 | 3582 |
| aac aca ccg ggc ttt tat gct cca tgg gaa gat ccc tcc ttt act tat<br>Asn Thr Pro Gly Phe Tyr Ala Pro Trp Glu Asp Pro Ser Phe Thr Tyr<br>               350              355             360 | 3630 |
| cca tca aat ttg gca cca cct tta cag att ctg ata gat tct agt aat<br>Pro Ser Asn Leu Ala Pro Pro Leu Gln Ile Leu Ile Asp Ser Ser Asn<br>        365              370              375 | 3678 |
| ggt gca tct gac tat ggg aac aaa ttt gga gag cca ttg atc cag ggt<br>Gly Ala Ser Asp Tyr Gly Asn Lys Phe Gly Glu Pro Leu Ile Gln Gly<br>            380              385             390 | 3726 |
| ttc tgt aga act ttc gga atg aga ctt cct ggt ggg gag agg cga gaa<br>Phe Cys Arg Thr Phe Gly Met Arg Leu Pro Gly Gly Glu Arg Arg Glu<br>395                400              405 | 3774 |
| tgg ttg aag cca atc atg ttc agc gca ggc ata gga cag att gac cac<br>Trp Leu Lys Pro Ile Met Phe Ser Ala Gly Ile Gly Gln Ile Asp His<br>410                415              420             425 | 3822 |
| ctt cat ata tca aag gga gag cct gac att ggg atg ctg gtt gtt aag<br>Leu His Ile Ser Lys Gly Glu Pro Asp Ile Gly Met Leu Val Val Lys<br>               430              435             440 | 3870 |
| att gga ggc ccg gct tat cgt att ggt atg gga ggt ggg gca gcc tca<br>Ile Gly Gly Pro Ala Tyr Arg Ile Gly Met Gly Gly Gly Ala Ala Ser<br>            445              450              455 | 3918 |
| agc atg gtc gat ggg cag aat gat gca gag ctt gat ttc aat gct gtg<br>Ser Met Val Asp Gly Gln Asn Asp Ala Glu Leu Asp Phe Asn Ala Val<br>460                465              470 | 3966 |
| caa cgt ggg gat gct gag atg gct caa aaa cta tat cgt ctt gtg cgt<br>Gln Arg Gly Asp Ala Glu Met Ala Gln Lys Leu Tyr Arg Leu Val Arg | 4014 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 475 |     |     |     |     | 480 |     |     |     |     | 485 |     |     |     |      |
| gct | tgt | att | gag | atg | ggg | gat | aaa | aac | cca | att | atc | agc | att | cat | gat | 4062 |
| Ala | Cys | Ile | Glu | Met | Gly | Asp | Lys | Asn | Pro | Ile | Ile | Ser | Ile | His | Asp |      |
| 490 |     |     |     | 495 |     |     |     |     | 500 |     |     |     |     | 505 |     |      |
| cag | gga | gct | ggt | ggg | aac | tgc | aat | gtt | gta | aag | gaa | att | ata | tat | ccg | 4110 |
| Gln | Gly | Ala | Gly | Gly | Asn | Cys | Asn | Val | Val | Lys | Glu | Ile | Ile | Tyr | Pro |      |
|     |     |     |     | 510 |     |     |     |     | 515 |     |     |     |     | 520 |     |      |
| aag | ggt | gct | gag | ata | gat | gtc | cga | gca | att | gtg | gtt | ggt | gat | cat | aca | 4158 |
| Lys | Gly | Ala | Glu | Ile | Asp | Val | Arg | Ala | Ile | Val | Val | Gly | Asp | His | Thr |      |
|     |     |     | 525 |     |     |     |     | 530 |     |     |     |     | 535 |     |     |      |
| atg | tct | gtt | cta | gaa | att | tgg | ggt | gca | gag | tat | cag | gag | cag | gat | gca | 4206 |
| Met | Ser | Val | Leu | Glu | Ile | Trp | Gly | Ala | Glu | Tyr | Gln | Glu | Gln | Asp | Ala |      |
|     |     | 540 |     |     |     |     | 545 |     |     |     |     | 550 |     |     |     |      |
| atc | tta | gtg | aag | cct | gaa | agc | cgt | gat | ctc | cta | gaa | tca | atc | tgt | aac | 4254 |
| Ile | Leu | Val | Lys | Pro | Glu | Ser | Arg | Asp | Leu | Leu | Glu | Ser | Ile | Cys | Asn |      |
|     | 555 |     |     |     |     | 560 |     |     |     |     | 565 |     |     |     |     |      |
| agg | gaa | aaa | gtt | tca | atg | gct | gtt | att | gga | act | atc | agt | gga | gat | gga | 4302 |
| Arg | Glu | Lys | Val | Ser | Met | Ala | Val | Ile | Gly | Thr | Ile | Ser | Gly | Asp | Gly |      |
| 570 |     |     |     |     | 575 |     |     |     |     | 580 |     |     |     |     | 585 |      |
| cgt | gtt | gtt | tta | gtt | gac | agt | gta | gca | gct | cag | aag | tct | att | tca | aat | 4350 |
| Arg | Val | Val | Leu | Val | Asp | Ser | Val | Ala | Ala | Gln | Lys | Ser | Ile | Ser | Asn |      |
|     |     |     |     | 590 |     |     |     |     | 595 |     |     |     |     | 600 |     |      |
| gga | ctc | cct | cca | cct | ccc | cct | gct | gtg | gat | ctt | gaa | ctg | gag | aaa | gtc | 4398 |
| Gly | Leu | Pro | Pro | Pro | Pro | Pro | Ala | Val | Asp | Leu | Glu | Leu | Glu | Lys | Val |      |
|     |     |     | 605 |     |     |     |     | 610 |     |     |     |     | 615 |     |     |      |
| ctt | ggt | gac | atg | cct | aag | aaa | act | ttt | aag | ttt | aat | cgg | gtt | gtt | tat | 4446 |
| Leu | Gly | Asp | Met | Pro | Lys | Lys | Thr | Phe | Lys | Phe | Asn | Arg | Val | Val | Tyr |      |
|     |     | 620 |     |     |     |     | 625 |     |     |     |     | 630 |     |     |     |      |
| gag | cgg | gag | cca | ctt | gat | att | gtc | cct | ggg | att | gaa | gtg | ata | gat | tct | 4494 |
| Glu | Arg | Glu | Pro | Leu | Asp | Ile | Val | Pro | Gly | Ile | Glu | Val | Ile | Asp | Ser |      |
|     | 635 |     |     |     |     | 640 |     |     |     |     | 645 |     |     |     |     |      |
| ctg | aag | agg | gta | ttg | agt | tta | ccg | tct | gtt | tgt | tca | aag | cgc | ttc | ttg | 4542 |
| Leu | Lys | Arg | Val | Leu | Ser | Leu | Pro | Ser | Val | Cys | Ser | Lys | Arg | Phe | Leu |      |
| 650 |     |     |     |     | 655 |     |     |     |     | 660 |     |     |     |     | 665 |      |
| aca | aca | aaa | gtt | gac | agg | tgt | gtt | act | ggt | cta | gtg | gca | caa | cag | caa | 4590 |
| Thr | Thr | Lys | Val | Asp | Arg | Cys | Val | Thr | Gly | Leu | Val | Ala | Gln | Gln | Gln |      |
|     |     |     |     | 670 |     |     |     |     | 675 |     |     |     |     | 680 |     |      |
| act | gtt | ggc | cct | ttg | cag | att | ccc | att | gct | gat | gtt | gct | gtt | aca | gct | 4638 |
| Thr | Val | Gly | Pro | Leu | Gln | Ile | Pro | Ile | Ala | Asp | Val | Ala | Val | Thr | Ala |      |
|     |     |     | 685 |     |     |     |     | 690 |     |     |     |     | 695 |     |     |      |
| caa | act | ttt | gct | gat | gtg | act | gga | ggt | gct | tgt | gcc | att | gga | gaa | caa | 4686 |
| Gln | Thr | Phe | Ala | Asp | Val | Thr | Gly | Gly | Ala | Cys | Ala | Ile | Gly | Glu | Gln |      |
|     |     | 700 |     |     |     |     | 705 |     |     |     |     | 710 |     |     |     |      |
| cca | atc | aaa | ggt | ttg | tta | gac | ccc | aaa | gca | atg | gct | cgg | ttg | gct | gtt | 4734 |
| Pro | Ile | Lys | Gly | Leu | Leu | Asp | Pro | Lys | Ala | Met | Ala | Arg | Leu | Ala | Val |      |
|     | 715 |     |     |     |     | 720 |     |     |     |     | 725 |     |     |     |     |      |
| gga | gaa | gca | cta | aca | aat | ctt | gta | tgg | gcg | aag | gtc | act | tcc | ctt | tct | 4782 |
| Gly | Glu | Ala | Leu | Thr | Asn | Leu | Val | Trp | Ala | Lys | Val | Thr | Ser | Leu | Ser |      |
| 730 |     |     |     |     | 735 |     |     |     |     | 740 |     |     |     |     | 745 |      |
| gat | gtc | aag | gct | agt | ggt | aac | tgg | atg | tat | gct | gcc | aag | ctt | gat | ggg | 4830 |
| Asp | Val | Lys | Ala | Ser | Gly | Asn | Trp | Met | Tyr | Ala | Ala | Lys | Leu | Asp | Gly |      |
|     |     |     |     | 750 |     |     |     |     | 755 |     |     |     |     | 760 |     |      |
| gaa | gga | gct | gac | atg | tat | gat | gct | gct | ata | tct | cta | tct | gaa | gca | atg | 4878 |
| Glu | Gly | Ala | Asp | Met | Tyr | Asp | Ala | Ala | Ile | Ser | Leu | Ser | Glu | Ala | Met |      |
|     |     |     | 765 |     |     |     |     | 770 |     |     |     |     | 775 |     |     |      |
| att | gaa | ctt | ggc | att | gct | att | gat | gga | ggg | aaa | gac | agt | ctt | tct | atg | 4926 |
| Ile | Glu | Leu | Gly | Ile | Ala | Ile | Asp | Gly | Gly | Lys | Asp | Ser | Leu | Ser | Met |      |
|     |     | 780 |     |     |     |     | 785 |     |     |     |     | 790 |     |     |     |      |
| gca | gcc | cac | gcc | gag | agt | gaa | gtt | gtc | aag | gct | ccg | gga | aat | ctt | gtc | 4974 |

```
Ala Ala His Ala Glu Ser Glu Val Val Lys Ala Pro Gly Asn Leu Val
    795                 800                 805 atc agt gtt tat gtt act tgt cct gat ata aca aaa aca gtg acg cca      5022
Ile Ser Val Tyr Val Thr Cys Pro Asp Ile Thr Lys Thr Val Thr Pro
810                 815                 820                 825 gat tta aaa ctc aag gat gat ggt att ttg ctt cat att gat ttg tca      5070
Asp Leu Lys Leu Lys Asp Asp Gly Ile Leu Leu His Ile Asp Leu Ser
                830                 835                 840 aaa ggt aag agg cgg tta ggt gga tct gct ctt gcc cag gca ttt gac      5118
Lys Gly Lys Arg Arg Leu Gly Gly Ser Ala Leu Ala Gln Ala Phe Asp
            845                 850                 855 caa gtt ggg aat gag tgt cct gat ctt gat gat gtt cct tac ctt aaa      5166
Gln Val Gly Asn Glu Cys Pro Asp Leu Asp Asp Val Pro Tyr Leu Lys
        860                 865                 870 aag gtc ttt gaa ggt gtt caa gac ctt ctt tct gat gaa ctg ata tct      5214
Lys Val Phe Glu Gly Val Gln Asp Leu Leu Ser Asp Glu Leu Ile Ser
    875                 880                 885 gct ggt cat gac atc agt gat ggt ggg ctg cta gtt tgt gcc tta gag      5262
Ala Gly His Asp Ile Ser Asp Gly Gly Leu Leu Val Cys Ala Leu Glu
890                 895                 900                 905 atg gca ttt gct ggt aat tgt gga ctt agt ttg gac ttt gca tcg caa      5310
Met Ala Phe Ala Gly Asn Cys Gly Leu Ser Leu Asp Phe Ala Ser Gln
                910                 915                 920 ggt aac agc ctt ttc caa aca ctc tat gct gaa gag ctt ggg tta gtt      5358
Gly Asn Ser Leu Phe Gln Thr Leu Tyr Ala Glu Glu Leu Gly Leu Val
            925                 930                 935 ctt gag gta agc aag aaa aat ctg gct ttg gta gtg aat aaa ttg agc      5406
Leu Glu Val Ser Lys Lys Asn Leu Ala Leu Val Val Asn Lys Leu Ser
        940                 945                 950 aat gtg gga gtt tct gct gaa atc ata ggt caa gta aca gcc aat cca      5454
Asn Val Gly Val Ser Ala Glu Ile Ile Gly Gln Val Thr Ala Asn Pro
    955                 960                 965 tca ata gaa gtt aag gtt gat ggg gag act tat tta act gaa aaa act      5502
Ser Ile Glu Val Lys Val Asp Gly Glu Thr Tyr Leu Thr Glu Lys Thr
970                 975                 980                 985 agt atc ctt agg gac atg tgg gaa gag acc agt ttt cag ctg gaa aag      5550
Ser Ile Leu Arg Asp Met Trp Glu Glu Thr Ser Phe Gln Leu Glu Lys
                990                 995                 1000 ttc caa agg ttg gca tct tgt gtg gat atg gag aaa gaa gga cta           5595
Phe Gln Arg Leu Ala Ser Cys Val Asp Met Glu Lys Glu Gly Leu
            1005                1010                1015 aaa cat cgt tat gaa ccc tca tgg gaa ctg cct ttt act cct tcc           5640
Lys His Arg Tyr Glu Pro Ser Trp Glu Leu Pro Phe Thr Pro Ser
            1020                1025                1030 ttc act gat gaa aag ctt tat gtc tgc aac tat aaa acc taa ag            5684
Phe Thr Asp Glu Lys Leu Tyr Val Cys Asn Tyr Lys Thr
            1035                1040

<210> SEQ ID NO 2
<211> LENGTH: 1044
<212> TYPE: PRT
<213> ORGANISM: Glycine max
<220> FEATURE:
<221> NAME/KEY: misc_feature
<222> LOCATION: (269)..(269)
<223> OTHER INFORMATION: The 'Xaa' at location 269 stands for Leu, or
      Phe.

<400> SEQUENCE: 2

Met Gln Glu Ser Ala Ala Ala Glu Leu Leu Lys Glu Ala Gln Val Lys
1               5                   10                  15
```

```
Ile Ser Ser Gln Ile Val Glu Ile Leu Thr Glu Gln Cys Tyr Asn Val
            20                  25                  30

Gly Leu Ser Ser Gln Leu Ser Gly Gly Lys Phe Ser Val Leu Gly Trp
         35                  40                  45

Leu Leu Gln Glu Thr Phe Glu Pro Glu Asn Leu Gly Thr Glu Ser Phe
     50                  55                  60

Leu Glu Lys Lys Arg Lys Glu Gly Leu Ile Pro Val Ile Val Glu Val
65                  70                  75                  80

Gly Pro Arg Leu Ser Phe Thr Thr Ala Trp Ser Thr Asn Ala Val Ala
             85                  90                  95

Ile Cys Gln Ala Cys Gly Leu Thr Glu Val Asn Arg Leu Glu Arg Ser
            100                 105                 110

Arg Arg Tyr Leu Leu Phe Thr Thr Thr Glu Leu Gln Asp Tyr Gln Ile
            115                 120                 125

Asn Asp Phe Ala Ser Met Val His Asp Arg Met Thr Glu Cys Val Tyr
130                 135                 140

Ile Gln Lys Leu Thr Ser Phe Glu Thr Ser Val Val Pro Glu Glu Ile
145                 150                 155                 160

His Tyr Ile Pro Val Met Glu Arg Gly Arg Lys Ala Leu Glu Glu Ile
                165                 170                 175

Asn Leu Glu Met Gly Phe Ala Phe Asp Asp Gln Asp Leu Glu Tyr Tyr
            180                 185                 190

Thr Lys Leu Phe Arg Glu Asp Ile Lys Arg Asn Pro Thr Asn Val Glu
         195                 200                 205

Leu Phe Asp Ile Ala Gln Ser Asn Ser Glu His Ser Arg His Trp Phe
     210                 215                 220

Phe Thr Gly Lys Ile Phe Ile Asp Gly Gln Pro Val Asn Arg Thr Leu
225                 230                 235                 240

Met Gln Ile Val Lys Ser Thr Leu Gln Ala Asn Pro Asn Asn Ser Val
             245                 250                 255

Ile Gly Phe Lys Asp Asn Ser Ser Ala Ile Arg Gly Xaa Pro Val Lys
            260                 265                 270

Gln Leu Arg Pro Val Gln Pro Gly Ser Ala Cys Pro Leu Glu Val Ala
            275                 280                 285

Val His Glu Leu Asp Ile Leu Phe Thr Ala Glu Thr His Asn Phe Pro
290                 295                 300

Cys Ala Val Ala Pro Tyr Pro Gly Ala Glu Thr Gly Ala Gly Gly Arg
305                 310                 315                 320

Ile Arg Asp Thr His Ala Thr Gly Arg Gly Ser Phe Val Gln Ala Ala
                325                 330                 335

Thr Ala Gly Tyr Cys Val Gly Asn Leu Asn Thr Pro Gly Phe Tyr Ala
            340                 345                 350

Pro Trp Glu Asp Pro Ser Phe Thr Tyr Pro Ser Asn Leu Ala Pro Pro
         355                 360                 365

Leu Gln Ile Leu Ile Asp Ser Ser Asn Gly Ala Ser Asp Tyr Gly Asn
     370                 375                 380

Lys Phe Gly Glu Pro Leu Ile Gln Gly Phe Cys Arg Thr Phe Gly Met
385                 390                 395                 400

Arg Leu Pro Gly Gly Glu Arg Arg Glu Trp Leu Lys Pro Ile Met Phe
            405                 410                 415

Ser Ala Gly Ile Gly Gln Ile Asp His Leu His Ile Ser Lys Gly Glu
            420                 425                 430

Pro Asp Ile Gly Met Leu Val Val Lys Ile Gly Gly Pro Ala Tyr Arg
```

-continued

```
                435                 440                 445
Ile Gly Met Gly Gly Ala Ala Ser Ser Met Val Asp Gly Gln Asn
    450                 455                 460

Asp Ala Glu Leu Asp Phe Asn Ala Val Gln Arg Gly Asp Ala Glu Met
465                 470                 475                 480

Ala Gln Lys Leu Tyr Arg Leu Val Arg Ala Cys Ile Glu Met Gly Asp
                485                 490                 495

Lys Asn Pro Ile Ile Ser Ile His Asp Gln Gly Ala Gly Gly Asn Cys
            500                 505                 510

Asn Val Val Lys Glu Ile Ile Tyr Pro Lys Gly Ala Glu Ile Asp Val
        515                 520                 525

Arg Ala Ile Val Val Gly Asp His Thr Met Ser Val Leu Glu Ile Trp
530                 535                 540

Gly Ala Glu Tyr Gln Glu Gln Asp Ala Ile Leu Val Lys Pro Glu Ser
545                 550                 555                 560

Arg Asp Leu Leu Glu Ser Ile Cys Asn Arg Glu Lys Val Ser Met Ala
                565                 570                 575

Val Ile Gly Thr Ile Ser Gly Asp Gly Arg Val Val Leu Val Asp Ser
            580                 585                 590

Val Ala Ala Gln Lys Ser Ile Ser Asn Gly Leu Pro Pro Pro Pro
        595                 600                 605

Ala Val Asp Leu Glu Leu Glu Lys Val Leu Gly Asp Met Pro Lys Lys
    610                 615                 620

Thr Phe Lys Phe Asn Arg Val Val Tyr Glu Arg Glu Pro Leu Asp Ile
625                 630                 635                 640

Val Pro Gly Ile Glu Val Ile Asp Ser Leu Lys Arg Val Leu Ser Leu
                645                 650                 655

Pro Ser Val Cys Ser Lys Arg Phe Leu Thr Thr Lys Val Asp Arg Cys
            660                 665                 670

Val Thr Gly Leu Val Ala Gln Gln Thr Val Gly Pro Leu Gln Ile
        675                 680                 685

Pro Ile Ala Asp Val Ala Val Thr Ala Gln Thr Phe Ala Asp Val Thr
    690                 695                 700

Gly Gly Ala Cys Ala Ile Gly Glu Gln Pro Ile Lys Gly Leu Leu Asp
705                 710                 715                 720

Pro Lys Ala Met Ala Arg Leu Ala Val Gly Glu Ala Leu Thr Asn Leu
                725                 730                 735

Val Trp Ala Lys Val Thr Ser Leu Ser Asp Val Lys Ala Ser Gly Asn
            740                 745                 750

Trp Met Tyr Ala Ala Lys Leu Asp Gly Glu Gly Ala Asp Met Tyr Asp
        755                 760                 765

Ala Ala Ile Ser Leu Ser Glu Ala Met Ile Glu Leu Gly Ile Ala Ile
    770                 775                 780

Asp Gly Gly Lys Asp Ser Leu Ser Met Ala Ala His Ala Glu Ser Glu
785                 790                 795                 800

Val Val Lys Ala Pro Gly Asn Leu Val Ile Ser Val Tyr Val Thr Cys
                805                 810                 815

Pro Asp Ile Thr Lys Thr Val Thr Pro Asp Leu Lys Leu Lys Asp Asp
            820                 825                 830

Gly Ile Leu Leu His Ile Asp Leu Ser Lys Gly Lys Arg Arg Leu Gly
        835                 840                 845

Gly Ser Ala Leu Ala Gln Ala Phe Asp Gln Val Gly Asn Glu Cys Pro
    850                 855                 860
```

-continued

```
Asp Leu Asp Asp Val Pro Tyr Leu Lys Lys Val Phe Glu Gly Val Gln
865                 870                 875                 880

Asp Leu Leu Ser Asp Glu Leu Ile Ser Ala Gly His Asp Ile Ser Asp
                885                 890                 895

Gly Gly Leu Leu Val Cys Ala Leu Glu Met Ala Phe Ala Gly Asn Cys
                900                 905                 910

Gly Leu Ser Leu Asp Phe Ala Ser Gln Gly Asn Ser Leu Phe Gln Thr
            915                 920                 925

Leu Tyr Ala Glu Glu Leu Gly Leu Val Leu Val Ser Lys Lys Asn
        930                 935                 940

Leu Ala Leu Val Val Asn Lys Leu Ser Asn Val Gly Val Ser Ala Glu
945                 950                 955                 960

Ile Ile Gly Gln Val Thr Ala Asn Pro Ser Ile Glu Val Lys Val Asp
                965                 970                 975

Gly Glu Thr Tyr Leu Thr Glu Lys Thr Ser Ile Leu Arg Asp Met Trp
            980                 985                 990

Glu Glu Thr Ser Phe Gln Leu Glu  Lys Phe Gln Arg Leu  Ala Ser Cys
        995                 1000                 1005

Val Asp  Met Glu Lys Glu Gly  Leu Lys His Arg Tyr  Glu Pro Ser
    1010                 1015                 1020

Trp Glu  Leu Pro Phe Thr Pro  Ser Phe Thr Asp Glu  Lys Leu Tyr
    1025                 1030                 1035

Val Cys  Asn Tyr Lys Thr
    1040
```

<210> SEQ ID NO 3
<211> LENGTH: 6450
<212> TYPE: DNA
<213> ORGANISM: Glycine max
<220> FEATURE:
<221> NAME/KEY: CDS
<222> LOCATION: (2484)..(6425)

<400> SEQUENCE: 3

```
ctcgagtgca ctttataaga atgtgtcagg tggattaaca attttgatag gatgtgataa      60
aaacagtctc attttaataa aacatttaa ataatatcat ttaataatt atttctaatt      120
ttggctcaaa tttatcaacc agttcaagaa gatcgtgaga ttttcatata tctattttat     180
ttcaatattt aaattgaaac tttcagttga tttttttttt gtcattcatt ttgtaatcaa     240
taaaattctt tgaatttgtt gagattgatt tctcttataa tatgatgaca ttatatttaa     300
ttttcttaa ttacaggttt ttcaataaca aaattggatt gttccttaaa aaattgaatt     360
gaaaaaaaa tgttgtcaca tagtaacttt tttttgaaa atgtcgtata gtaacttgca      420
ctttacaaat caaggacata aattaatttt agcataagtt tggctatgca ttttaaaaa     480
atagatcaac gtctaatgca aaagccactc ccgcaactca caagtttctg aatcttttgg   540
gaatttaatg tgaaaatgag agaatcaacc gataagaatt ttttatatat atttcaatta   600
agatgtgaag attattattg aagtagacac atgataagat agaaaatata cttataaaag   660
aaaataaata atatgcagat gaattatctc actcaagtaa aaatctaaac ttattatata   720
agaatgaatt ttatatttta tgtagctata gaagataatt tatcttgaga tatttttaatt   780
cattaattat taatttaacg atttcaactt tttataaacc acaggcaatt tgatagagac   840
gttaaaactt taaaagaaaa atccaaattg tacttacggt tcccacaggc ccaattctac   900
ctagagttta ttgaagagcc aattctattt tgttttcctc ccataaaatc aaatacacct   960
```

-continued

```
tttttgataa aagttttttt ttttatctag attacataag agataatctc ttttgatttt      1020
tttatagaga aatatctttc gaattaaata tctaaaagtc acttttttact gcatttaaaa     1080 gtcatataat gcactaaata ttatatataa ttaaaggata tcttgctttt atcttatttt      1140
atcatattct ttgtcaaatt ctctcttatt aaacaaaatt ttaataataa tttgggaata     1200
aataataata taattttttaa cacaagacta attttatgat cttatattaa tacaagttaa    1260
ctatagttga aaatgctttt tttttttttta cggaatactt gaaaatactt cttaaaataa   1320
taagtaggaa tatatcgtgt aaatttgttt aaatttattc tataaaaaat acttatttta    1380
ataaaataaa caattttttt ttcttttttta gtgtttgttt aaatcgtttt tacctatttt   1440 attttttcttg ttttaaaaaa aatcttatct attttatgtaa aaagcattta aaaaacactt  1500
actttaaatt aaaaaatatt aatactagct tttagttttt tttttttataa gatatcttac   1560 caatttacag cttcgagttt cacaaagaaa ctagtgtgtt tatactgaca aagctcttat    1620
cggcgtctgt tatgaacttt ggataacgca tccgattcgg attcggctaa aagtaagcat    1680
cagcagacaa agaaattgtc gataaaacag aggaaggaga attaaaatat ataaagtagc   1740
gccaacgcaa ccaatagttg aattgaaagg ttgaaaactt tttatatttt attggtttga   1800
ttggaacttg gaagggaaag aaagagagta ccaagtggct agtagggttt tattttgtgc   1860
cacaccaaaa ccctctcttc gttttacgcc actgccacac tctgttttgt tctggtattc   1920
ttcgattcta cttcttcttc ttgattctca ctatactcat tgtgccacag ttctgattgt   1980
gcttagtgat tctttctcaa gctttttttt ttttttttttt aatttattta gagctttccc  2040
tacacttgtt cgaggacatg gcggctgcga cggaatttgg ggtgtcgcaa ttcttgcagg  2100
tttgatttta atccctctct ttgaattaac atcatatgct gctgcacccc ttttattaat   2160
ttattaattg ctgctcttgt tgggggaaaa agtttcatgc tttgatgctg tttggttttg   2220 tgatttttggt ttcaggtacc tccaggcaaa ctctgttttt gaagaagaag ccacagagac  2280
agagaagaag catgtttttgg ggtgcgctct ggaataggaa ttgggctctg ggatcaactc 2340
acagagcttt gcctttaagg tgccaggctc aggaaaatcc cagagctgta gtttctggtg  2400
gcgtgagcag ttctgtagag gagcaacctg ccttggttga aagcccgct tccgaagttg   2460 ttcatttgta tcgtgtcccg ttt atg caa gca agt gca gct gct gag ctt ttg   2513
                        Met Gln Ala Ser Ala Ala Ala Glu Leu Leu
                         1               5                  10 aag gaa gct caa gtg aaa atc tcc ggt cag atc gtg gaa ata cag act     2561
Lys Glu Ala Gln Val Lys Ile Ser Gly Gln Ile Val Glu Ile Gln Thr
             15                  20                  25 gag cag tgt tat aat gtt ggc ctt agt tca caa ctt tct ggt gga aaa     2609
Glu Gln Cys Tyr Asn Val Gly Leu Ser Ser Gln Leu Ser Gly Gly Lys
         30                  35                  40 ttt tcg gtc ctt aga tgg ctt ctt caa gaa aca ttt gag cct gag aat     2657
Phe Ser Val Leu Arg Trp Leu Leu Gln Glu Thr Phe Glu Pro Glu Asn
     45                  50                  55 ctg gga act gag agc ttt ctt gag aag aag aag aaa gag ggt ctg agt     2705
Leu Gly Thr Glu Ser Phe Leu Glu Lys Lys Lys Lys Glu Gly Leu Ser
 60                  65                  70 cca gtt att gtt gaa gtt ggc ccc agg ctg tca ttt acc acg gca tgg     2753
Pro Val Ile Val Glu Val Gly Pro Arg Leu Ser Phe Thr Thr Ala Trp
 75                  80                  85                  90 tct acc aat gct gtt gca att tgc caa gcc tgt ggt ttg aca gaa gtg     2801
Ser Thr Asn Ala Val Ala Ile Cys Gln Ala Cys Gly Leu Thr Glu Val
                 95                 100                 105
```

```
aac cgt ttg gaa cgg tcc agg agg tac ttg ttg ttc acc acc act gaa    2849
Asn Arg Leu Glu Arg Ser Arg Arg Tyr Leu Leu Phe Thr Thr Thr Glu
        110                 115                 120 ctg caa gat tat caa atc aat gat ttt acg tct atg gtg cat gat agg    2897
Leu Gln Asp Tyr Gln Ile Asn Asp Phe Thr Ser Met Val His Asp Arg
    125                 130                 135 atg act gaa tgt gtt tat gtt cag aag cta aca tcc ttc gag act agt    2945
Met Thr Glu Cys Val Tyr Val Gln Lys Leu Thr Ser Phe Glu Thr Ser
140                 145                 150 gtt gtt cca gag gag att cgt tat ata cct gtc atg gag aag ggg cga    2993
Val Val Pro Glu Glu Ile Arg Tyr Ile Pro Val Met Glu Lys Gly Arg
155                 160                 165                 170 aag gca tta gaa gag att aat ctg gag atg ggt ttt gcc ttt gat gac    3041
Lys Ala Leu Glu Glu Ile Asn Leu Glu Met Gly Phe Ala Phe Asp Asp
            175                 180                 185 cag gat ttg gaa tac tac acc aaa ctc ttc agg gaa gac att aag cgt    3089
Gln Asp Leu Glu Tyr Tyr Thr Lys Leu Phe Arg Glu Asp Ile Lys Arg
        190                 195                 200 aac cca aca aat gtg gaa ttg ttt gat att gcg cag tcc aac agt gag    3137
Asn Pro Thr Asn Val Glu Leu Phe Asp Ile Ala Gln Ser Asn Ser Glu
    205                 210                 215 cac agc aga cac tgg ttt ttt act gga aat att ttc att gat gga cag    3185
His Ser Arg His Trp Phe Phe Thr Gly Asn Ile Phe Ile Asp Gly Gln
220                 225                 230 cct gtg aat aga act ctc atg cag att gtg aaa agt act ctg cag gca    3233
Pro Val Asn Arg Thr Leu Met Gln Ile Val Lys Ser Thr Leu Gln Ala
235                 240                 245                 250 aac cca aat aac tca gtt att ggc ttc aag gat aac tcg agt gca atg    3281
Asn Pro Asn Asn Ser Val Ile Gly Phe Lys Asp Asn Ser Ser Ala Met
            255                 260                 265 cag ggg ttt tcc agt gaa gca gct ccg acc agt tca acc tgg ttc aac    3329
Gln Gly Phe Ser Ser Glu Ala Ala Pro Thr Ser Ser Thr Trp Phe Asn
        270                 275                 280 ttg tcc att aga agt tgc agt cat gag tta gat atc ttg ttt aca gcc    3377
Leu Ser Ile Arg Ser Cys Ser His Glu Leu Asp Ile Leu Phe Thr Ala
    285                 290                 295 gaa aca cat aat ttt cca tgt gca gtg gca cct tat cct ggt gca gag    3425
Glu Thr His Asn Phe Pro Cys Ala Val Ala Pro Tyr Pro Gly Ala Glu
300                 305                 310 aca ggt gca gga ggt cgt att agg gat aca cat gct aca gga agg ggg    3473
Thr Gly Ala Gly Gly Arg Ile Arg Asp Thr His Ala Thr Gly Arg Gly
315                 320                 325                 330 tcc ttt gtc caa gca gct aca gct ggt tat tgc gtt ggg aat ctc aac    3521
Ser Phe Val Gln Ala Ala Thr Ala Gly Tyr Cys Val Gly Asn Leu Asn
            335                 340                 345 aca cca ggc ttt tat gct cca tgg gaa gat tcc tcc ttt act tat cca    3569
Thr Pro Gly Phe Tyr Ala Pro Trp Glu Asp Ser Ser Phe Thr Tyr Pro
        350                 355                 360 tca aat ttg gca cca cct tta cag att ctg ata gat tct agt aat ggt    3617
Ser Asn Leu Ala Pro Pro Leu Gln Ile Leu Ile Asp Ser Ser Asn Gly
    365                 370                 375 gca tct gac tat ggg aac aaa ttt gga gag cca ttg atc cag ggt ttc    3665
Ala Ser Asp Tyr Gly Asn Lys Phe Gly Glu Pro Leu Ile Gln Gly Phe
380                 385                 390 tgt aga act ttt gga atg aga ctt ccc agt ggg gag agg cga gaa tgg    3713
Cys Arg Thr Phe Gly Met Arg Leu Pro Ser Gly Glu Arg Arg Glu Trp
395                 400                 405                 410 ttg aag cct atc atg ttc agc gca ggc att gga cag att gac cac ctt    3761
Leu Lys Pro Ile Met Phe Ser Ala Gly Ile Gly Gln Ile Asp His Leu
            415                 420                 425
```

-continued

| | |
|---|---|
| cat ata tca aag gga gag cct gac att ggg atg ctg gtt gtt aag att<br>His Ile Ser Lys Gly Glu Pro Asp Ile Gly Met Leu Val Val Lys Ile<br>430 435 440 | 3809 |
| gga ggc ccg gct tat cgt att ggt atg gga ggc ggg gca gcc tca agc<br>Gly Gly Pro Ala Tyr Arg Ile Gly Met Gly Gly Gly Ala Ala Ser Ser<br>445 450 455 | 3857 |
| atg gtc agt ggg cag aat gat gca gag ctt gat ttc aat gct gtg caa<br>Met Val Ser Gly Gln Asn Asp Ala Glu Leu Asp Phe Asn Ala Val Gln<br>460 465 470 | 3905 |
| cgt ggg gat gct gag atg gct caa aaa cta tat cgt ctt gtg cgt gct<br>Arg Gly Asp Ala Glu Met Ala Gln Lys Leu Tyr Arg Leu Val Arg Ala<br>475 480 485 490 | 3953 |
| tgt att gag atg ggg gat aaa aac cca att atc agc att cat gat cag<br>Cys Ile Glu Met Gly Asp Lys Asn Pro Ile Ile Ser Ile His Asp Gln<br>495 500 505 | 4001 |
| gga gct ggt ggg aat tgc aat gtt gta aag gaa att ata tat cca aag<br>Gly Ala Gly Gly Asn Cys Asn Val Val Lys Glu Ile Ile Tyr Pro Lys<br>510 515 520 | 4049 |
| ggt gct gag ata gat gtt cga gca att gtg gtt ggc gat cat aca atg<br>Gly Ala Glu Ile Asp Val Arg Ala Ile Val Val Gly Asp His Thr Met<br>525 530 535 | 4097 |
| tct gtt cta gaa att tgg ggt gca gag tat cag gag cag gat gca atc<br>Ser Val Leu Glu Ile Trp Gly Ala Glu Tyr Gln Glu Gln Asp Ala Ile<br>540 545 550 | 4145 |
| ttg gtg aag cct gaa agt cgt gat ctt ctg gaa tca atc tgt aac agg<br>Leu Val Lys Pro Glu Ser Arg Asp Leu Leu Glu Ser Ile Cys Asn Arg<br>555 560 565 570 | 4193 |
| gag aaa gtt tca atg gct gtt att gga act atc agt ggt gat gga cgt<br>Glu Lys Val Ser Met Ala Val Ile Gly Thr Ile Ser Gly Asp Gly Arg<br>575 580 585 | 4241 |
| gtt gtt tta gtt gac agt gta gca gtc cag aag tct att tca aat gga<br>Val Val Leu Val Asp Ser Val Ala Val Gln Lys Ser Ile Ser Asn Gly<br>590 595 600 | 4289 |
| ctc act tca cct ccc cct gcc gtg gat ctt gaa ttg gag aaa gtc ctt<br>Leu Thr Ser Pro Pro Pro Ala Val Asp Leu Glu Leu Glu Lys Val Leu<br>605 610 615 | 4337 |
| ggt gac atg cct aag aaa act ttt aaa ttt aat cgg gtt gtt tat gag<br>Gly Asp Met Pro Lys Lys Thr Phe Lys Phe Asn Arg Val Val Tyr Glu<br>620 625 630 | 4385 |
| agg gag cca ctt gat att gcc cct ggg att gaa gtg ata gat tcc cta<br>Arg Glu Pro Leu Asp Ile Ala Pro Gly Ile Glu Val Ile Asp Ser Leu<br>635 640 645 650 | 4433 |
| aag agg gta ttg agt tta ccg tct gtt tgt tca aag cgc ttc tta aca<br>Lys Arg Val Leu Ser Leu Pro Ser Val Cys Ser Lys Arg Phe Leu Thr<br>655 660 665 | 4481 |
| aca aaa gtt gat agg tgt gtt act ggt cta gtg gca caa caa caa act<br>Thr Lys Val Asp Arg Cys Val Thr Gly Leu Val Ala Gln Gln Gln Thr<br>670 675 680 | 4529 |
| gtt ggc cct ttg cag att ccc att gct gat gtt gct gtt aca gct caa<br>Val Gly Pro Leu Gln Ile Pro Ile Ala Asp Val Ala Val Thr Ala Gln<br>685 690 695 | 4577 |
| act ttt gtt gat gtg act gga ggt gct tgt gcc att ggt gag caa ccc<br>Thr Phe Val Asp Val Thr Gly Gly Ala Cys Ala Ile Gly Glu Gln Pro<br>700 705 710 | 4625 |
| atc aaa ggc ctg tta gac ccc aaa gca atg gct cgg ttg gct gtt gga<br>Ile Lys Gly Leu Leu Asp Pro Lys Ala Met Ala Arg Leu Ala Val Gly<br>715 720 725 730 | 4673 |
| gaa gca cta aca aat ctt gta tgg gca aag gtc act tcc ctt tct gat<br>Glu Ala Leu Thr Asn Leu Val Trp Ala Lys Val Thr Ser Leu Ser Asp | 4721 |

```
                735                 740                 745
gtc aag gct agt ggt aac tgg atg tat gct gcc aag ctt gat ggg gaa       4769
Val Lys Ala Ser Gly Asn Trp Met Tyr Ala Ala Lys Leu Asp Gly Glu
            750                 755                 760 gga gct gac atg tat gat gca gct ata tct cta tct gaa gca atg att       4817
Gly Ala Asp Met Tyr Asp Ala Ala Ile Ser Leu Ser Glu Ala Met Ile
        765                 770                 775 gaa ctt ggc att gct att gat gga ggg aaa gac agc ctt tct atg gca       4865
Glu Leu Gly Ile Ala Ile Asp Gly Gly Lys Asp Ser Leu Ser Met Ala
    780                 785                 790 gcc cac gct gaa agt gaa gtt gtc aag gca cca ggr aat ctt gtc atc       4913
Ala His Ala Glu Ser Glu Val Val Lys Ala Pro Xaa Asn Leu Val Ile
795                 800                 805                 810 agt gtk tat gtt act tgt cct gat ata aca aaa aca gtg act cca gat       4961
Ser Xaa Tyr Val Thr Cys Pro Asp Ile Thr Lys Thr Val Thr Pro Asp
            815                 820                 825 tta aaa ctc aag gat gat ggt att ttg ctt cat att gat ttg tca aaa       5009
Leu Lys Leu Lys Asp Asp Gly Ile Leu Leu His Ile Asp Leu Ser Lys
        830                 835                 840 ggt aag agg cgg tta ggt gga tct gct ctt gcc cag gcg ttt gac caa       5057
Gly Lys Arg Arg Leu Gly Gly Ser Ala Leu Ala Gln Ala Phe Asp Gln
    845                 850                 855 gtt gga gat gag tgt cct gat cct gat gat gtt cct tac ctt aaa aag       5105
Val Gly Asp Glu Cys Pro Asp Pro Asp Asp Val Pro Tyr Leu Lys Lys
860                 865                 870 gcc ttt gaa ggt gtt caa gac ctt ctt tct gat gaa ttg ata tct gct       5153
Ala Phe Glu Gly Val Gln Asp Leu Leu Ser Asp Glu Leu Ile Ser Ala
875                 880                 885                 890 ggt cat gac atc agt gat ggt ggg ctg cta gtt tgt gcc tta gag atg       5201
Gly His Asp Ile Ser Asp Gly Gly Leu Leu Val Cys Ala Leu Glu Met
            895                 900                 905 gca ttt gct ggt aac tgt ggt ctt agt ttg gac ttg gcg tcg caa ggt       5249
Ala Phe Ala Gly Asn Cys Gly Leu Ser Leu Asp Leu Ala Ser Gln Gly
        910                 915                 920 acc agc ctt ttc caa aca ctc tat gct gaa gag ctt ggg tta gtt ctt       5297
Thr Ser Leu Phe Gln Thr Leu Tyr Ala Glu Glu Leu Gly Leu Val Leu
    925                 930                 935 gag gta aac aag aaa aat ctg gct ttg gta atg gat aaa ttg agt aat       5345
Glu Val Asn Lys Lys Asn Leu Ala Leu Val Met Asp Lys Leu Ser Asn
940                 945                 950 gtg gga gtt tca gct gaa atc att ggt caa gta aca gcc aat cca tca       5393
Val Gly Val Ser Ala Glu Ile Ile Gly Gln Val Thr Ala Asn Pro Ser
955                 960                 965                 970 ata gaa gtt aag gtt gat ggg gag act tat tta act gaa aaa act agt       5441
Ile Glu Val Lys Val Asp Gly Glu Thr Tyr Leu Thr Glu Lys Thr Ser
            975                 980                 985 atc ctt agg gac ttg tgg gaa gag acc agt ttt cag ctg gaa aag ttc       5489
Ile Leu Arg Asp Leu Trp Glu Glu Thr Ser Phe Gln Leu Glu Lys Phe
        990                 995                 1000 caa aga ttg gca tcc tgt gtg gat atg gag aaa gaa gga ctt aaa           5534
Gln Arg Leu Ala Ser Cys Val Asp Met Glu Lys Glu Gly Leu Lys
    1005                1010                1015 cat cga tat gag ccc tca tgg gaa ctg cct ttt act ccc acc ttc           5579
His Arg Tyr Glu Pro Ser Trp Glu Leu Pro Phe Thr Pro Thr Phe
    1020                1025                1030 act gat gga aag ctt ctg tct gca act ata aaa cct aaa gtg gct           5624
Thr Asp Gly Lys Leu Leu Ser Ala Thr Ile Lys Pro Lys Val Ala
    1035                1040                1045 gtg att aga gaa gaa ggc agt aat gga gac aga gaa atg gct gca           5669
```

```
                                             -continued
Val Ile Arg Glu Glu Gly Ser Asn Gly Asp Arg Glu Met Ala Ala
        1050                1055                1060 gca ttt tat gct gct ggt ttt gaa cca tgg gat att act atg tca       5714
Ala Phe Tyr Ala Ala Gly Phe Glu Pro Trp Asp Ile Thr Met Ser
        1065                1070                1075 gac ctt ctt aat gga aag atc tct ttg caa gac ttc cgc gga att       5759
Asp Leu Leu Asn Gly Lys Ile Ser Leu Gln Asp Phe Arg Gly Ile
        1080                1085                1090 gtg ttt gtt ggt gga ttt agc tat gct gat gtg ctt gat tct gca       5804
Val Phe Val Gly Gly Phe Ser Tyr Ala Asp Val Leu Asp Ser Ala
        1095                1100                1105 aaa ggt tgg tct gct agc ata aga ttc aat gag tcc gtt tta caa       5849
Lys Gly Trp Ser Ala Ser Ile Arg Phe Asn Glu Ser Val Leu Gln
        1110                1115                1120 caa ttt cag gag ttt tac aag cgt cca gac act ttc agt ctc ggt       5894
Gln Phe Gln Glu Phe Tyr Lys Arg Pro Asp Thr Phe Ser Leu Gly
        1125                1130                1135 gta tgc aat gga tgt cag cta atg gct ttg ttg gga tgg gta ccg       5939
Val Cys Asn Gly Cys Gln Leu Met Ala Leu Leu Gly Trp Val Pro
        1140                1145                1150 ggt cca caa gtt ggg ggt gtg cat ggt gct ggt ggc gac cta tca       5984
Gly Pro Gln Val Gly Gly Val His Gly Ala Gly Gly Asp Leu Ser
        1155                1160                1165 caa ccg agg ttc att cat aat gag tca ggg cgg ttt gag tgc cgc       6029
Gln Pro Arg Phe Ile His Asn Glu Ser Gly Arg Phe Glu Cys Arg
        1170                1175                1180 ttt aca agt gtg acc ata aag gac tca ccg gct ata atg ttc aaa       6074
Phe Thr Ser Val Thr Ile Lys Asp Ser Pro Ala Ile Met Phe Lys
        1185                1190                1195 gac atg gca ggt agc aca ttg ggt ata tgg gct gct cat ggt gag       6119
Asp Met Ala Gly Ser Thr Leu Gly Ile Trp Ala Ala His Gly Glu
        1200                1205                1210 gga aga gct tat ttc cca gat gaa ggc gtg ttg gac cgt ata gtt       6164
Gly Arg Ala Tyr Phe Pro Asp Glu Gly Val Leu Asp Arg Ile Val
        1215                1220                1225 cat tct gag ttg gct cct ata aga tac tgt gat gat gct ggg aat       6209
His Ser Glu Leu Ala Pro Ile Arg Tyr Cys Asp Asp Ala Gly Asn
        1230                1235                1240 cca aca gag gcc tac cct ttc aat gtg aat ggc tct cct tta ggg       6254
Pro Thr Glu Ala Tyr Pro Phe Asn Val Asn Gly Ser Pro Leu Gly
        1245                1250                1255 gtg gca gct att tgt tcc cca gat ggg agg cat ctt gcc atg atg       6299
Val Ala Ala Ile Cys Ser Pro Asp Gly Arg His Leu Ala Met Met
        1260                1265                1270 cct cat cct gag cgt tgc ttc tta atg tgg cag ttc cca tgg tat       6344
Pro His Pro Glu Arg Cys Phe Leu Met Trp Gln Phe Pro Trp Tyr
        1275                1280                1285 cca aag cag tgg gat gtg gag aag aag ggg cct agt cct tgg tta       6389
Pro Lys Gln Trp Asp Val Glu Lys Lys Gly Pro Ser Pro Trp Leu
        1290                1295                1300 cgc atg ttc cag aat gca aga gag tgg tgt tcc tga aatgatcaaa       6435
Arg Met Phe Gln Asn Ala Arg Glu Trp Cys Ser
        1305                1310 tgttttctc atctt                                                   6450

<210> SEQ ID NO 4
<211> LENGTH: 1313
<212> TYPE: PRT
<213> ORGANISM: Glycine max
<220> FEATURE:
```

-continued

```
<221> NAME/KEY: misc_feature
<222> LOCATION: (806)..(806)
<223> OTHER INFORMATION: The 'Xaa' at location 806 stands for Gly.
<220> FEATURE:
<221> NAME/KEY: misc_feature
<222> LOCATION: (812)..(812)
<223> OTHER INFORMATION: The 'Xaa' at location 812 stands for Val.

<400> SEQUENCE: 4
```

Met Gln Ala Ser Ala Ala Glu Leu Leu Lys Glu Ala Gln Val Lys
1               5                   10                  15

Ile Ser Gly Gln Ile Val Glu Ile Gln Thr Glu Gln Cys Tyr Asn Val
            20                  25                  30

Gly Leu Ser Ser Gln Leu Ser Gly Gly Lys Phe Ser Val Leu Arg Trp
            35                  40                  45

Leu Leu Gln Glu Thr Phe Glu Pro Glu Asn Leu Gly Thr Glu Ser Phe
50                  55                  60

Leu Glu Lys Lys Lys Lys Glu Gly Leu Ser Pro Val Ile Val Glu Val
65                  70                  75                  80

Gly Pro Arg Leu Ser Phe Thr Thr Ala Trp Ser Thr Asn Ala Val
                85                  90                  95

Ile Cys Gln Ala Cys Gly Leu Thr Glu Val Asn Arg Leu Glu Arg Ser
                100                 105                 110

Arg Arg Tyr Leu Leu Phe Thr Thr Glu Leu Gln Asp Tyr Gln Ile
                115                 120                 125

Asn Asp Phe Thr Ser Met Val His Asp Arg Met Thr Glu Cys Val Tyr
                130                 135                 140

Val Gln Lys Leu Thr Ser Phe Glu Thr Ser Val Val Pro Glu Glu Ile
145                 150                 155                 160

Arg Tyr Ile Pro Val Met Glu Lys Gly Arg Lys Ala Leu Glu Glu Ile
                165                 170                 175

Asn Leu Glu Met Gly Phe Ala Phe Asp Asp Gln Asp Leu Glu Tyr Tyr
                180                 185                 190

Thr Lys Leu Phe Arg Glu Asp Ile Lys Arg Asn Pro Thr Asn Val Glu
                195                 200                 205

Leu Phe Asp Ile Ala Gln Ser Asn Ser Glu His Ser Arg His Trp Phe
210                 215                 220

Phe Thr Gly Asn Ile Phe Ile Asp Gly Gln Pro Val Asn Arg Thr Leu
225                 230                 235                 240

Met Gln Ile Val Lys Ser Thr Leu Gln Ala Asn Pro Asn Asn Ser Val
                245                 250                 255

Ile Gly Phe Lys Asp Asn Ser Ser Ala Met Gln Gly Phe Ser Ser Glu
                260                 265                 270

Ala Ala Pro Thr Ser Ser Thr Trp Phe Asn Leu Ser Ile Arg Ser Cys
                275                 280                 285

Ser His Glu Leu Asp Ile Leu Phe Thr Ala Glu Thr His Asn Phe Pro
                290                 295                 300

Cys Ala Val Ala Pro Tyr Pro Gly Ala Glu Thr Gly Ala Gly Gly Arg
305                 310                 315                 320

Ile Arg Asp Thr His Ala Thr Gly Arg Gly Ser Phe Val Gln Ala Ala
                325                 330                 335

Thr Ala Gly Tyr Cys Val Gly Asn Leu Asn Thr Pro Gly Phe Tyr Ala
                340                 345                 350

Pro Trp Glu Asp Ser Ser Phe Thr Tyr Pro Ser Asn Leu Ala Pro Pro
                355                 360                 365

```
Leu Gln Ile Leu Ile Asp Ser Ser Asn Gly Ala Ser Asp Tyr Gly Asn
    370                 375                 380
Lys Phe Gly Glu Pro Leu Ile Gln Gly Phe Cys Arg Thr Phe Gly Met
385                 390                 395                 400
Arg Leu Pro Ser Gly Glu Arg Arg Glu Trp Leu Lys Pro Ile Met Phe
            405                 410                 415
Ser Ala Gly Ile Gly Gln Ile Asp His Leu His Ile Ser Lys Gly Glu
                420                 425                 430
Pro Asp Ile Gly Met Leu Val Val Lys Ile Gly Gly Pro Ala Tyr Arg
            435                 440                 445
Ile Gly Met Gly Gly Ala Ser Ser Met Val Ser Gly Gln Asn
    450                 455                 460
Asp Ala Glu Leu Asp Phe Asn Ala Val Gln Arg Gly Asp Ala Glu Met
465                 470                 475                 480
Ala Gln Lys Leu Tyr Arg Leu Val Arg Ala Cys Ile Glu Met Gly Asp
                485                 490                 495
Lys Asn Pro Ile Ile Ser Ile His Asp Gln Gly Ala Gly Asn Cys
            500                 505                 510
Asn Val Val Lys Glu Ile Ile Tyr Pro Lys Gly Ala Glu Ile Asp Val
        515                 520                 525
Arg Ala Ile Val Val Gly Asp His Thr Met Ser Val Leu Glu Ile Trp
530                 535                 540
Gly Ala Glu Tyr Gln Glu Gln Asp Ala Ile Leu Val Lys Pro Glu Ser
545                 550                 555                 560
Arg Asp Leu Leu Glu Ser Ile Cys Asn Arg Glu Lys Val Ser Met Ala
                565                 570                 575
Val Ile Gly Thr Ile Ser Gly Asp Gly Arg Val Val Leu Val Asp Ser
            580                 585                 590
Val Ala Val Gln Lys Ser Ile Ser Asn Gly Leu Thr Ser Pro Pro Pro
        595                 600                 605
Ala Val Asp Leu Glu Leu Glu Lys Val Leu Gly Asp Met Pro Lys Lys
    610                 615                 620
Thr Phe Lys Phe Asn Arg Val Val Tyr Glu Arg Glu Pro Leu Asp Ile
625                 630                 635                 640
Ala Pro Gly Ile Glu Val Ile Asp Ser Leu Lys Arg Val Leu Ser Leu
            645                 650                 655
Pro Ser Val Cys Ser Lys Arg Phe Leu Thr Thr Lys Val Asp Arg Cys
                660                 665                 670
Val Thr Gly Leu Val Ala Gln Gln Thr Val Gly Pro Leu Gln Ile
            675                 680                 685
Pro Ile Ala Asp Val Ala Val Thr Ala Gln Thr Phe Val Asp Val Thr
    690                 695                 700
Gly Gly Ala Cys Ala Ile Gly Glu Gln Pro Ile Lys Gly Leu Leu Asp
705                 710                 715                 720
Pro Lys Ala Met Ala Arg Leu Ala Val Gly Glu Ala Leu Thr Asn Leu
            725                 730                 735
Val Trp Ala Lys Val Thr Ser Leu Ser Asp Val Lys Ala Ser Gly Asn
                740                 745                 750
Trp Met Tyr Ala Ala Lys Leu Asp Gly Glu Gly Ala Asp Met Tyr Asp
            755                 760                 765
Ala Ala Ile Ser Leu Ser Glu Ala Met Ile Glu Leu Gly Ile Ala Ile
    770                 775                 780
Asp Gly Gly Lys Asp Ser Leu Ser Met Ala Ala His Ala Glu Ser Glu
```

-continued

```
              785                 790                 795                 800
Val Val Lys Ala Pro Xaa Asn Leu Val Ile Ser Xaa Tyr Val Thr Cys
                    805                 810                 815

Pro Asp Ile Thr Lys Thr Val Thr Pro Asp Leu Lys Leu Lys Asp Asp
                820                 825                 830

Gly Ile Leu Leu His Ile Asp Leu Ser Lys Gly Lys Arg Arg Leu Gly
            835                 840                 845

Gly Ser Ala Leu Ala Gln Ala Phe Asp Gln Val Gly Asp Glu Cys Pro
        850                 855                 860

Asp Pro Asp Asp Val Pro Tyr Leu Lys Lys Ala Phe Glu Gly Val Gln
865                 870                 875                 880

Asp Leu Leu Ser Asp Glu Leu Ile Ser Ala Gly His Asp Ile Ser Asp
                885                 890                 895

Gly Gly Leu Leu Val Cys Ala Leu Glu Met Ala Phe Ala Gly Asn Cys
                900                 905                 910

Gly Leu Ser Leu Asp Leu Ala Ser Gln Gly Thr Ser Leu Phe Gln Thr
            915                 920                 925

Leu Tyr Ala Glu Glu Leu Gly Leu Val Leu Glu Val Asn Lys Lys Asn
        930                 935                 940

Leu Ala Leu Val Met Asp Lys Leu Ser Asn Val Gly Val Ser Ala Glu
945                 950                 955                 960

Ile Ile Gly Gln Val Thr Ala Asn Pro Ser Ile Glu Val Lys Val Asp
                965                 970                 975

Gly Glu Thr Tyr Leu Thr Glu Lys Thr Ser Ile Leu Arg Asp Leu Trp
            980                 985                 990

Glu Glu Thr Ser Phe Gln Leu Glu Lys Phe Gln Arg Leu Ala Ser Cys
        995                 1000                1005

Val Asp Met Glu Lys Glu Gly Leu Lys His Arg Tyr Glu Pro Ser
1010                1015                1020

Trp Glu Leu Pro Phe Thr Pro Thr Phe Thr Asp Gly Lys Leu Leu
1025                1030                1035

Ser Ala Thr Ile Lys Pro Lys Val Ala Val Ile Arg Glu Glu Gly
1040                1045                1050

Ser Asn Gly Asp Arg Glu Met Ala Ala Ala Phe Tyr Ala Ala Gly
1055                1060                1065

Phe Glu Pro Trp Asp Ile Thr Met Ser Asp Leu Leu Asn Gly Lys
1070                1075                1080

Ile Ser Leu Gln Asp Phe Arg Gly Ile Val Phe Val Gly Gly Phe
1085                1090                1095

Ser Tyr Ala Asp Val Leu Asp Ser Ala Lys Gly Trp Ser Ala Ser
1100                1105                1110

Ile Arg Phe Asn Glu Ser Val Leu Gln Gln Phe Gln Glu Phe Tyr
1115                1120                1125

Lys Arg Pro Asp Thr Phe Ser Leu Gly Val Cys Asn Gly Cys Gln
1130                1135                1140

Leu Met Ala Leu Leu Gly Trp Val Pro Gly Pro Gln Val Gly Gly
1145                1150                1155

Val His Gly Ala Gly Gly Asp Leu Ser Gln Pro Arg Phe Ile His
1160                1165                1170

Asn Glu Ser Gly Arg Phe Glu Cys Arg Phe Thr Ser Val Thr Ile
1175                1180                1185

Lys Asp Ser Pro Ala Ile Met Phe Lys Asp Met Ala Gly Ser Thr
1190                1195                1200
```

```
Leu Gly  Ile Trp Ala Ala His  Gly Glu Gly Arg Ala  Tyr Phe Pro
    1205             1210                 1215

Asp Glu  Gly Val Leu Asp Arg  Ile Val His Ser Glu  Leu Ala Pro
    1220             1225                 1230

Ile Arg  Tyr Cys Asp Asp Ala  Gly Asn Pro Thr Glu  Ala Tyr Pro
    1235             1240                 1245

Phe Asn  Val Asn Gly Ser Pro  Leu Gly Val Ala Ala  Ile Cys Ser
    1250             1255                 1260

Pro Asp  Gly Arg His Leu Ala  Met Met Pro His Pro  Glu Arg Cys
    1265             1270                 1275

Phe Leu  Met Trp Gln Phe Pro  Trp Tyr Pro Lys Gln  Trp Asp Val
    1280             1285                 1290

Glu Lys  Lys Gly Pro Ser Pro  Trp Leu Arg Met Phe  Gln Asn Ala
    1295             1300                 1305

Arg Glu  Trp Cys Ser
    1310

<210> SEQ ID NO 5
<211> LENGTH: 60
<212> TYPE: PRT
<213> ORGANISM: Drosophila melanogaster

<400> SEQUENCE: 5

Pro Phe Ser Gly Ala Thr Thr Gly Thr Gly Gly Arg Leu Arg Asp Val
1               5                   10                  15

Gln Gly Val Gly Arg Gly Gly Val Pro Ile Ala Gly Thr Ala Gly Tyr
            20                  25                  30

Cys Val Gly Ala Leu His Ile Pro Gly Tyr Lys Gln Pro Tyr Glu Pro
        35                  40                  45

Leu Asp Phe Lys Tyr Pro Ala Thr Phe Ala Pro Pro
    50                  55                  60

<210> SEQ ID NO 6
<211> LENGTH: 60
<212> TYPE: PRT
<213> ORGANISM: Homo sapiens

<400> SEQUENCE: 6

Pro Phe Ser Gly Ala Thr Thr Gly Thr Gly Gly Arg Ile Arg Asp Val
1               5                   10                  15

Gln Cys Thr Gly Arg Gly Ala His Val Val Ala Gly Thr Ala Gly Tyr
            20                  25                  30

Cys Phe Gly Asn Leu His Ile Pro Gly Tyr Asn Leu Pro Trp Glu Asp
        35                  40                  45

Leu Ser Phe Gln Tyr Pro Gly Asn Phe Ala Arg Pro
    50                  55                  60

<210> SEQ ID NO 7
<211> LENGTH: 59
<212> TYPE: PRT
<213> ORGANISM: Escherichia coli

<400> SEQUENCE: 7

Pro Trp Pro Gly Ala Ala Thr Gly Ser Gly Gly Glu Ile Arg Asp Glu
1               5                   10                  15

Gly Ala Thr Gly Arg Gly Ala Lys Pro Lys Ala Gly Leu Val Gly Phe
            20                  25                  30
```

-continued

```
Ser Val Ser Asn Leu Arg Ile Pro Gly Phe Glu Gln Pro Trp Glu Glu
            35                  40                  45

Asp Phe Gly Lys Pro Glu Arg Ile Val Thr Ala
    50                  55

<210> SEQ ID NO 8
<211> LENGTH: 60
<212> TYPE: PRT
<213> ORGANISM: Drosophila melanogaster

<400> SEQUENCE: 8

Glu Glu Gly Val Asn Ser Glu Arg Glu Met Met Ala Cys Leu Leu Arg
1               5                   10                  15

Ala Asn Phe Glu Val His Asp Val Thr Met Ser Asp Leu Leu Gln Gly
            20                  25                  30

Thr Ala Ser Val Ser Gln Tyr Arg Gly Leu Ile Phe Pro Gly Gly Phe
        35                  40                  45

Ser Tyr Ala Asp Thr Leu Gly Ser Ala Lys Gly Trp
    50                  55                  60

<210> SEQ ID NO 9
<211> LENGTH: 60
<212> TYPE: PRT
<213> ORGANISM: Homo sapiens

<400> SEQUENCE: 9

Glu Glu Gly Ser Asn Gly Asp Arg Glu Met Ala Asp Ala Phe His Leu
1               5                   10                  15

Ala Gly Phe Glu Val Trp Asp Val Thr Met Gln Asp Leu Cys Ser Gly
            20                  25                  30

Ala Ile Gly Leu Asp Thr Phe Arg Gly Val Ala Phe Val Gly Gly Phe
        35                  40                  45

Ser Tyr Ala Asp Val Leu Gly Ser Ala Lys Gly Trp
    50                  55                  60

<210> SEQ ID NO 10
<211> LENGTH: 60
<212> TYPE: PRT
<213> ORGANISM: Escherichia coli

<400> SEQUENCE: 10

Glu Gln Gly Val Asn Ser His Val Glu Met Ala Ala Ala Phe His Arg
1               5                   10                  15

Ala Gly Phe Asp Ala Ile Asp Val His Met Ser Asp Leu Leu Thr Gly
            20                  25                  30

Arg Thr Gly Leu Glu Asp Phe His Ala Leu Val Ala Cys Gly Gly Phe
        35                  40                  45

Ser Tyr Gly Asp Val Leu Gly Ala Gly Glu Gly Trp
    50                  55                  60

<210> SEQ ID NO 11
<211> LENGTH: 52
<212> TYPE: PRT
<213> ORGANISM: Drosophila melanogaster

<400> SEQUENCE: 11

Ala Ala Asn Ile Leu His Asn Pro Arg Leu Leu Pro Gln Phe Glu Ala
1               5                   10                  15

Phe Lys Arg Arg Gln Asp Val Phe Ser Leu Gly Ile Cys Asn Gly Cys
            20                  25                  30
```

```
Gln Leu Met Thr Leu Ile Gly Phe Val Gly Ser Ala Lys Ser Glu Val
        35                  40                  45

Gly Ala Asp Pro
    50

<210> SEQ ID NO 12
<211> LENGTH: 60
<212> TYPE: PRT
<213> ORGANISM: Homo sapiens

<400> SEQUENCE: 12

Ala Ala Ala Val Thr Phe His Pro Arg Ala Gly Ala Glu Leu Arg Arg
1               5                   10                  15

Phe Arg Lys Arg Pro Asp Thr Phe Ser Leu Gly Val Cys Asn Gly Cys
            20                  25                  30

Gln Leu Leu Ala Leu Leu Gly Trp Val Gly Gly Asp Pro Asn Glu Asp
        35                  40                  45

Ala Ala Glu Met Gly Pro Asp Ser Gln Pro Ala Arg
    50                  55                  60

<210> SEQ ID NO 13
<211> LENGTH: 48
<212> TYPE: PRT
<213> ORGANISM: Escherichia coli

<400> SEQUENCE: 13

Ala Lys Ser Ile Leu Phe Asn Asp Arg Val Arg Asp Glu Phe Ala Thr
1               5                   10                  15

Phe Phe His Arg Pro Gln Thr Leu Ala Leu Gly Val Cys Asn Gly Cys
            20                  25                  30

Gln Met Met Ser Asn Leu Arg Glu Leu Ile Pro Gly Ser Glu Leu Trp
        35                  40                  45

<210> SEQ ID NO 14
<211> LENGTH: 60
<212> TYPE: PRT
<213> ORGANISM: Drosophila melanogaster

<400> SEQUENCE: 14

Gln Ser Glu Gln Leu Val Thr Leu Gln Tyr Val Asp Asp Val Gly Lys
1               5                   10                  15

Pro Thr Glu Leu Tyr Pro Leu Asn Pro Asn Gly Ser Pro Gln Gly Ile
            20                  25                  30

Ala Gly Leu Cys Ser Ser Asp Gly Arg His Leu Ala Leu Met Pro His
        35                  40                  45

Pro Glu Arg Cys Ser Ser Met Tyr Gln Trp Pro Tyr
    50                  55                  60

<210> SEQ ID NO 15
<211> LENGTH: 60
<212> TYPE: PRT
<213> ORGANISM: Homo sapiens

<400> SEQUENCE: 15

Glu Ala Arg Gly Leu Ala Pro Leu His Trp Ala Asp Asp Gly Asn
1               5                   10                  15

Pro Thr Glu Gln Tyr Pro Leu Asn Pro Asn Gly Ser Pro Gly Gly Val
            20                  25                  30

Ala Gly Ile Cys Ser Cys Asp Gly Arg His Leu Ala Val Met Pro His
```

```
                      35                  40                  45
Pro Glu Arg Ala Val Arg Pro Trp Gln Trp Ala Trp
    50                  55                  60

<210> SEQ ID NO 16
<211> LENGTH: 60
<212> TYPE: PRT
<213> ORGANISM: Escherichia coli

<400> SEQUENCE: 16

Glu Ser Lys Gly Leu Val Ala Leu Arg Tyr Val Asp Asn Phe Gly Lys
1               5                  10                  15

Val Thr Glu Thr Tyr Pro Ala Asn Pro Asn Gly Ser Pro Asn Gly Ile
            20                  25                  30

Thr Ala Val Thr Thr Glu Ser Gly Arg Val Thr Ile Met Met Pro His
            35                  40                  45

Pro Glu Arg Val Phe Arg Thr Val Ser Asn Ser Trp
    50                  55                  60

<210> SEQ ID NO 17
<211> LENGTH: 37
<212> TYPE: DNA
<213> ORGANISM: Solanum tuberosum

<400> SEQUENCE: 17
aaccgatata tatatatata tatatatata tatatat                              37

<210> SEQ ID NO 18
<211> LENGTH: 83
<212> TYPE: DNA
<213> ORGANISM: Solanum tuberosum

<400> SEQUENCE: 18
atatcgttaa aatattttaa tatcttgttg aaatataatt ttttatttag taaaataata    60
tgagaattaa ttttttttat taa                                            83
```